(12) United States Patent
Munoz et al.

(10) Patent No.: US 7,426,476 B2
(45) Date of Patent: Sep. 16, 2008

(54) SYSTEM AND METHOD FOR AUTOMATED PRESCRIPTION MANAGEMENT

(75) Inventors: Michael A. Munoz, Derby, CT (US);
Emre Oksan, Mount Prospect, IL (US);
David R. Munoz, Tacoma, WA (US)

(73) Assignee: Whittier Group Inc., Las Vegas, NV (US)

( * ) Notice: Subject to any disclaimer, the term of this patent is extended or adjusted under 35 U.S.C. 154(b) by 1051 days.

(21) Appl. No.: 09/818,168

(22) Filed: Mar. 27, 2001

(65) Prior Publication Data

US 2002/0052760 A1   May 2, 2002

(51) Int. Cl.
*G06Q 50/00* (2006.01)

(52) U.S. Cl. .............................. 705/3; 705/2
(58) Field of Classification Search .............. 705/2, 705/3; 221/2; 235/380; 600/300
See application file for complete search history.

(56) References Cited

U.S. PATENT DOCUMENTS

| | | | | |
|---|---|---|---|---|
| 4,766,542 A | * | 8/1988 | Pilarczyk | 705/3 |
| 5,845,255 A | * | 12/1998 | Mayaud | 705/3 |
| 5,935,060 A | * | 8/1999 | Iliff | 600/300 |
| 6,022,315 A | * | 2/2000 | Iliff | 600/300 |
| 6,032,155 A | * | 2/2000 | de la Huerga | 707/104.1 |
| 6,421,650 B1 | * | 7/2002 | Goetz et al. | 705/3 |
| 6,493,427 B1 | * | 12/2002 | Kobylevsky et al. | 379/67.1 |

OTHER PUBLICATIONS

Chandler, Michele. 1999. E-health's catching; Medical sites get robust investment :[Metro Edition]. San Antonio Express-News, Aug. 9.*
ProxyMed Announces General Release of its Prescribe 2000 Physician Desktop Prescription Management System. 1999. PR Newswire Jun. 16.*
Rockport Healthcare Group Secures Absolute Data's CompCareRx(R) to Provide Workers' Compensation Pharmacy Benefits. 1999. PR Newswire Jul. 27.*

* cited by examiner

*Primary Examiner*—James P. Trammell
*Assistant Examiner*—Martin A. Gottschalk
(74) *Attorney, Agent, or Firm*—Fitch, Even, Tabin & Flannery

(57) ABSTRACT

An automated Triage Administrator system that links data for prescription requests, prescription refill requests, medical history requests and a patient's prescription history in a data base. The system allows pharmacies and physicians access to the desired medical information by fax or internet protocols. The system also provides all newly issued and current prescriptions to be joined into one "Super Prescription" for convenient distribution.

17 Claims, 22 Drawing Sheets

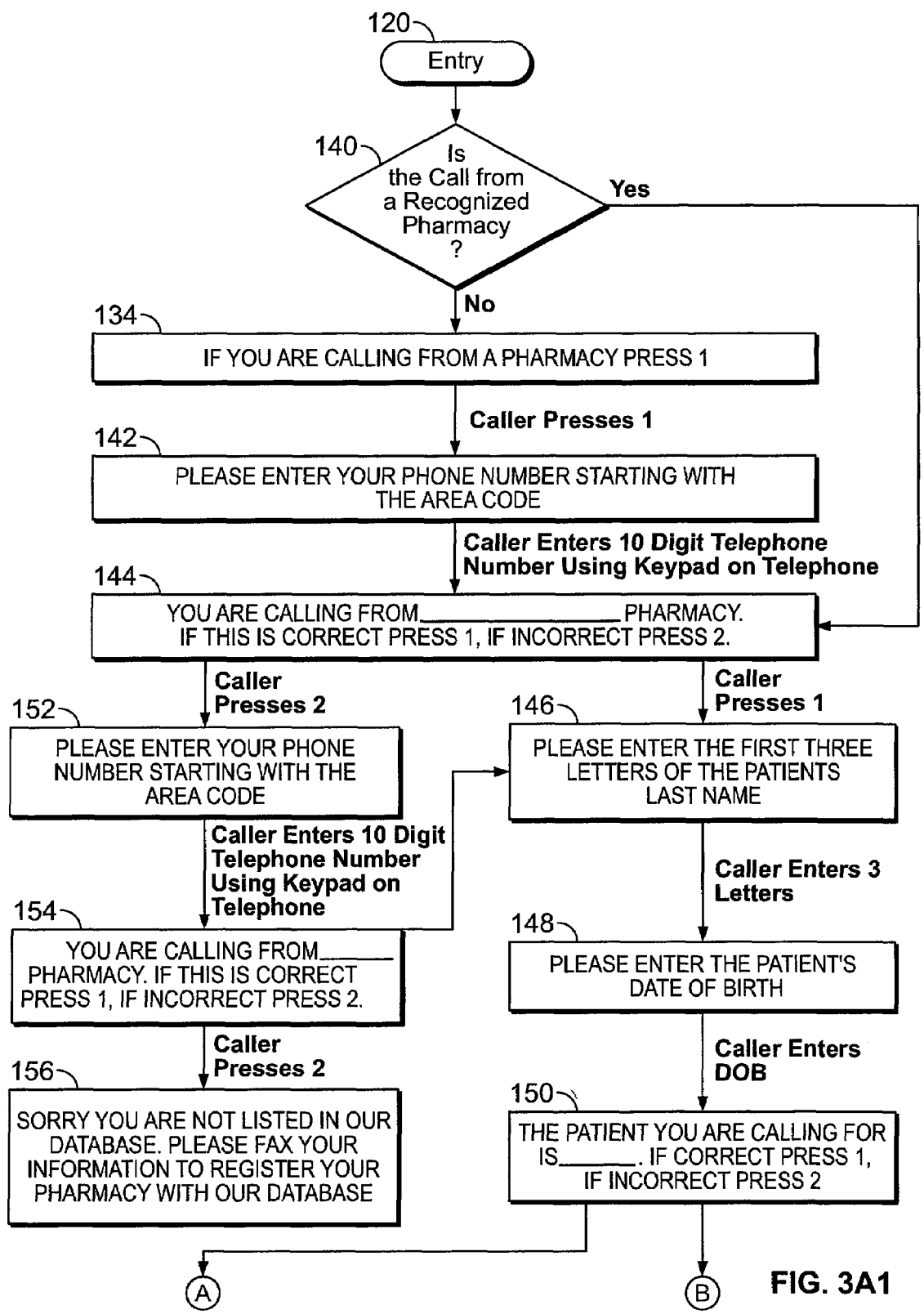
FIG. 3A1

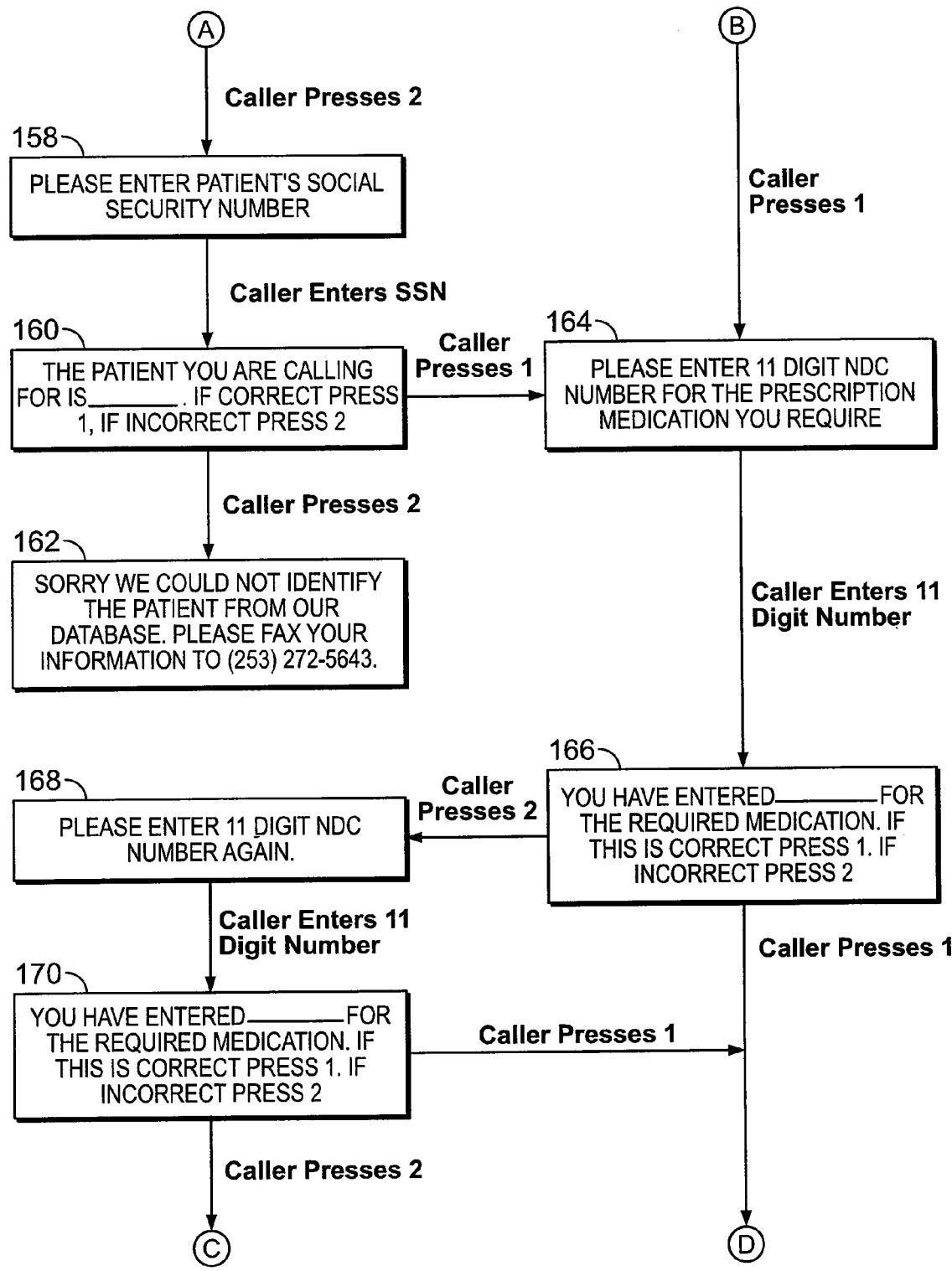
FIG. 3A2

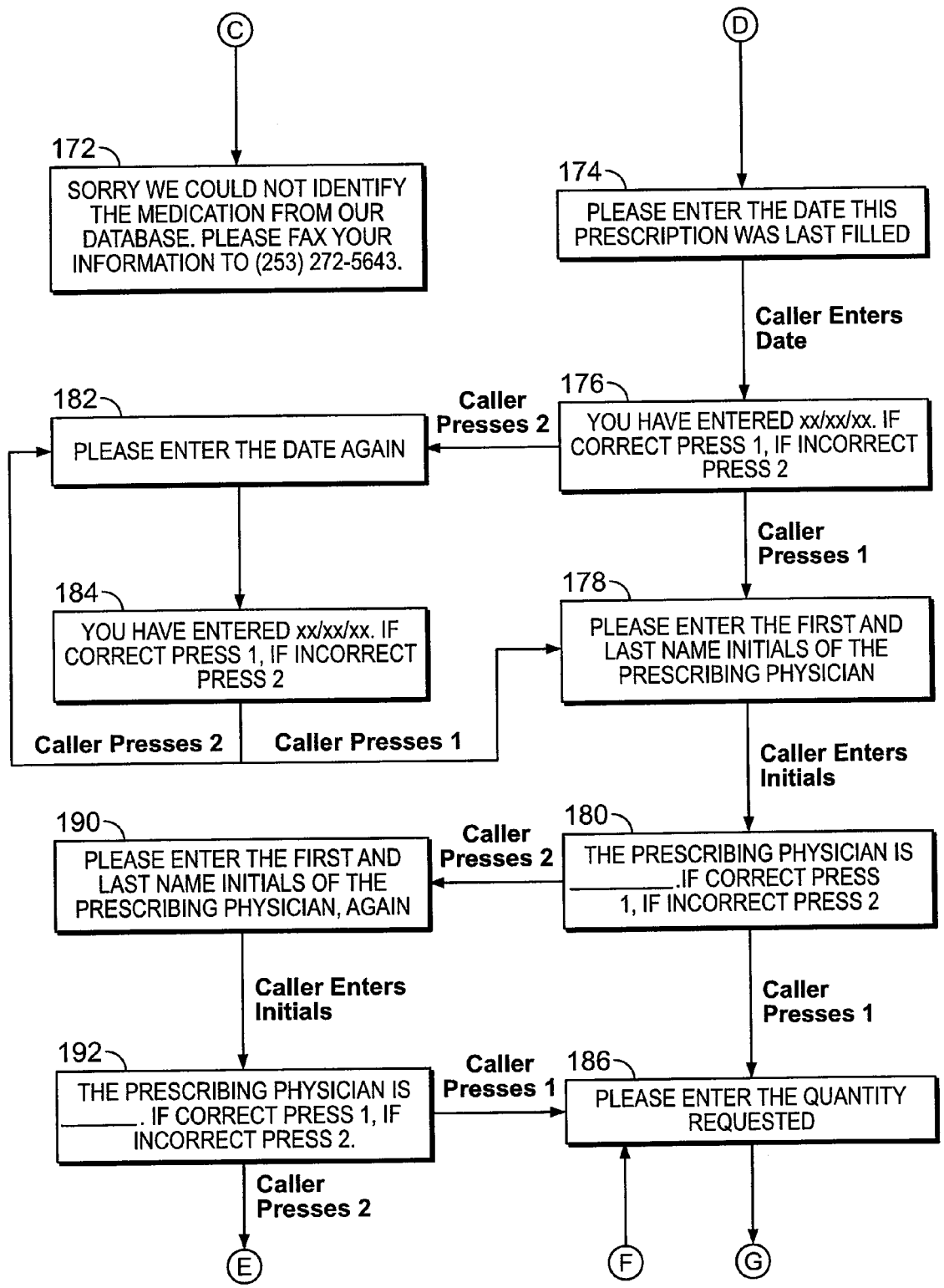
FIG. 3B1

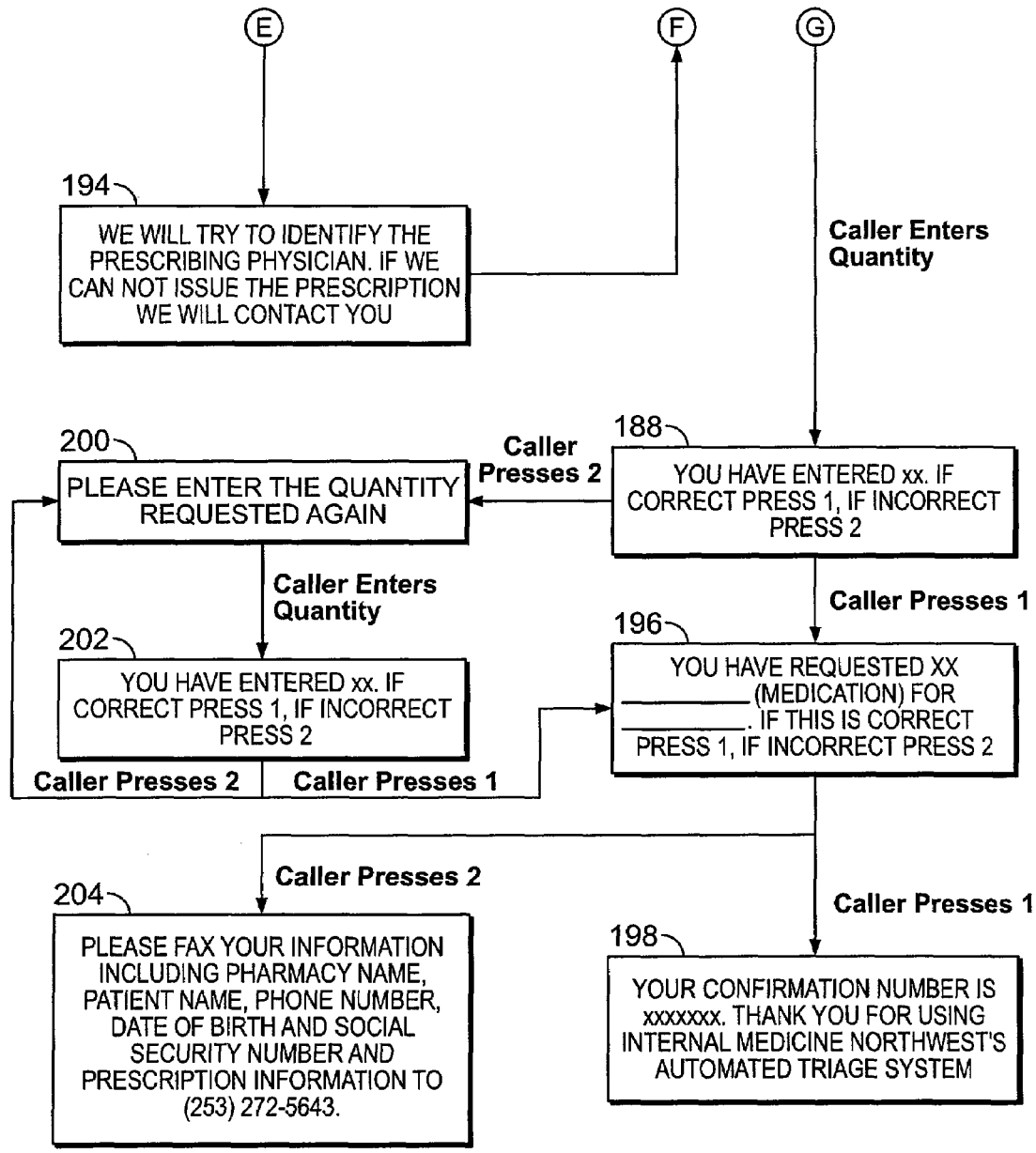
FIG. 3B2

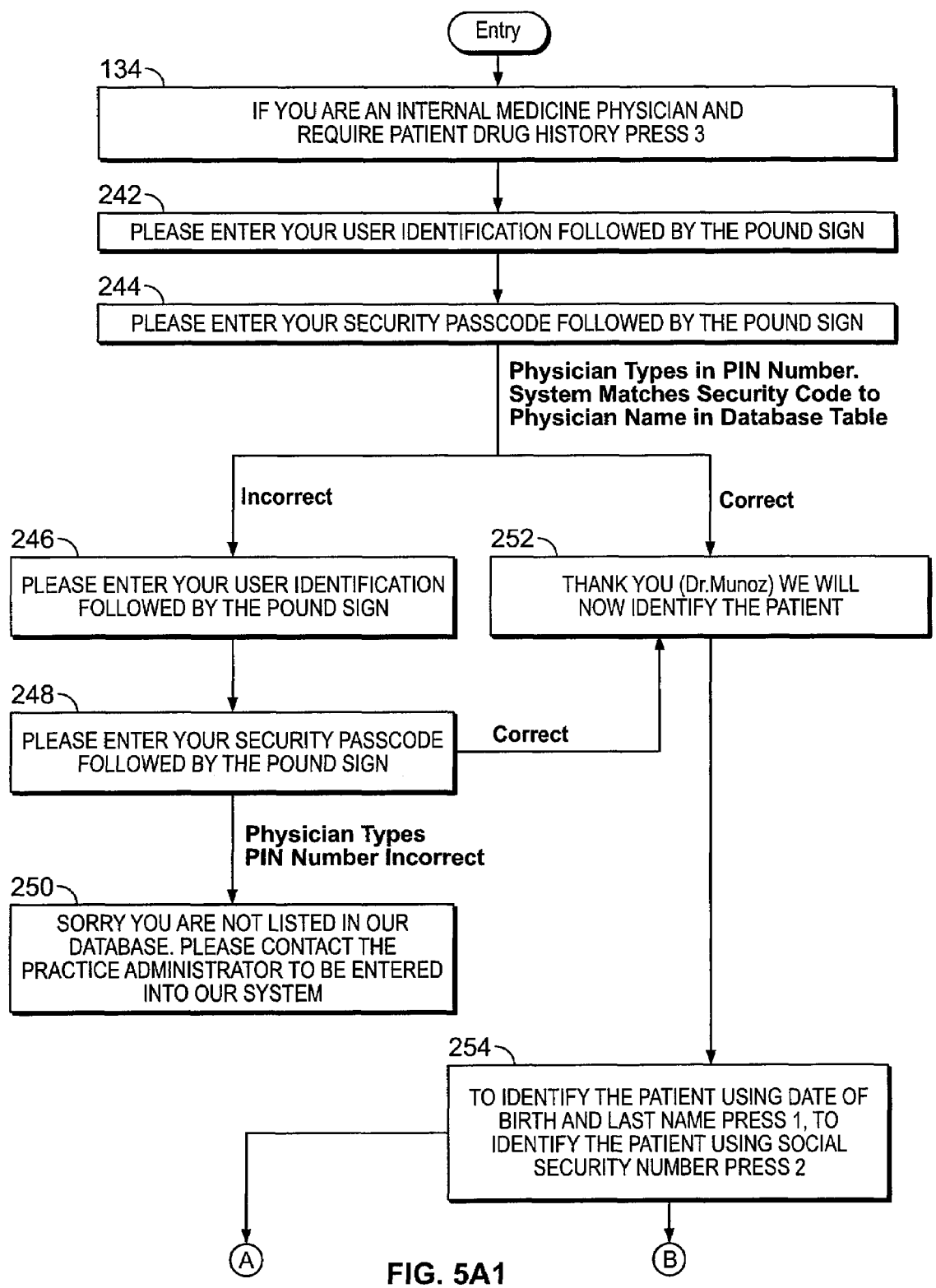
FIG. 5A1

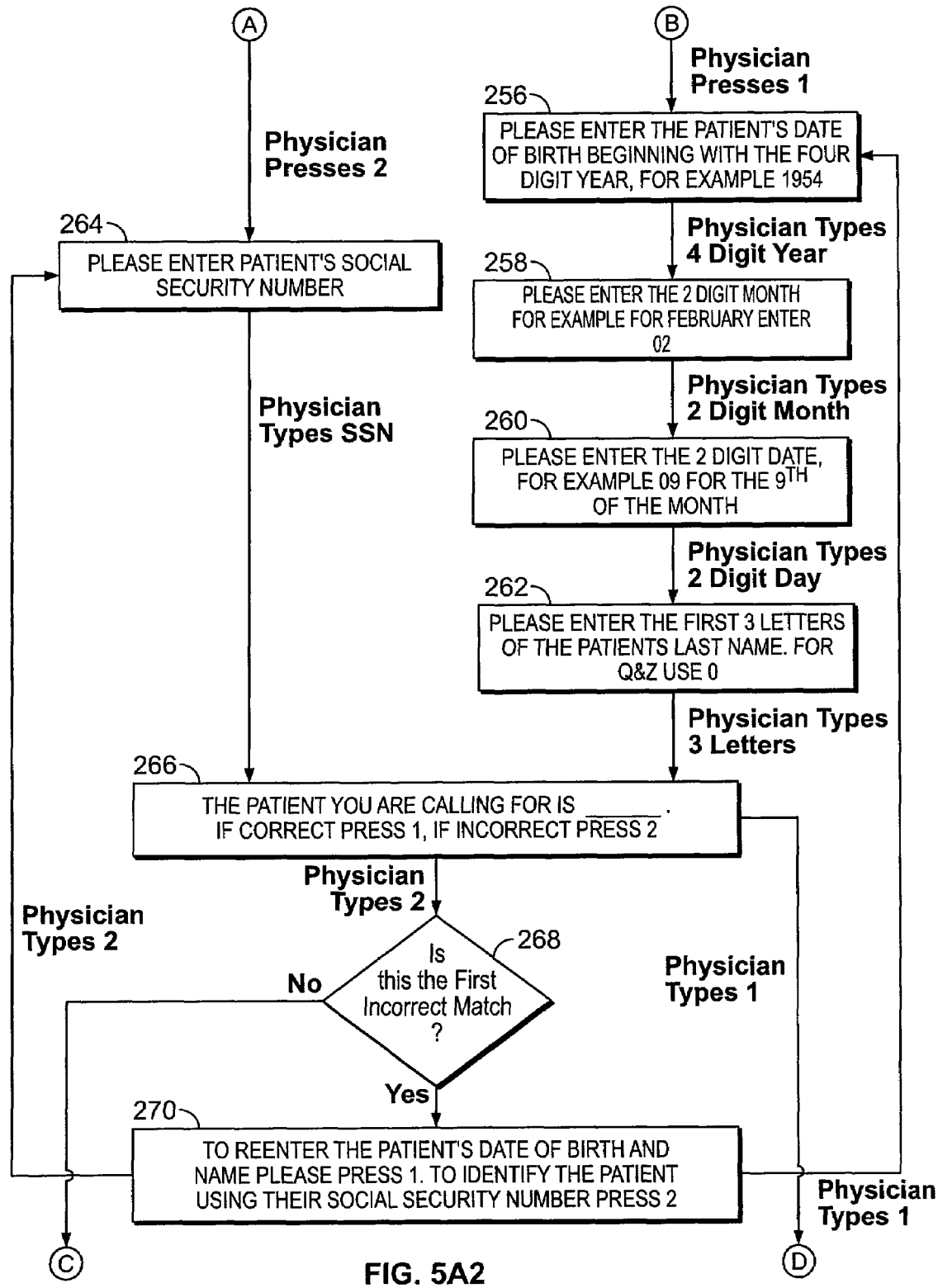
FIG. 5A2

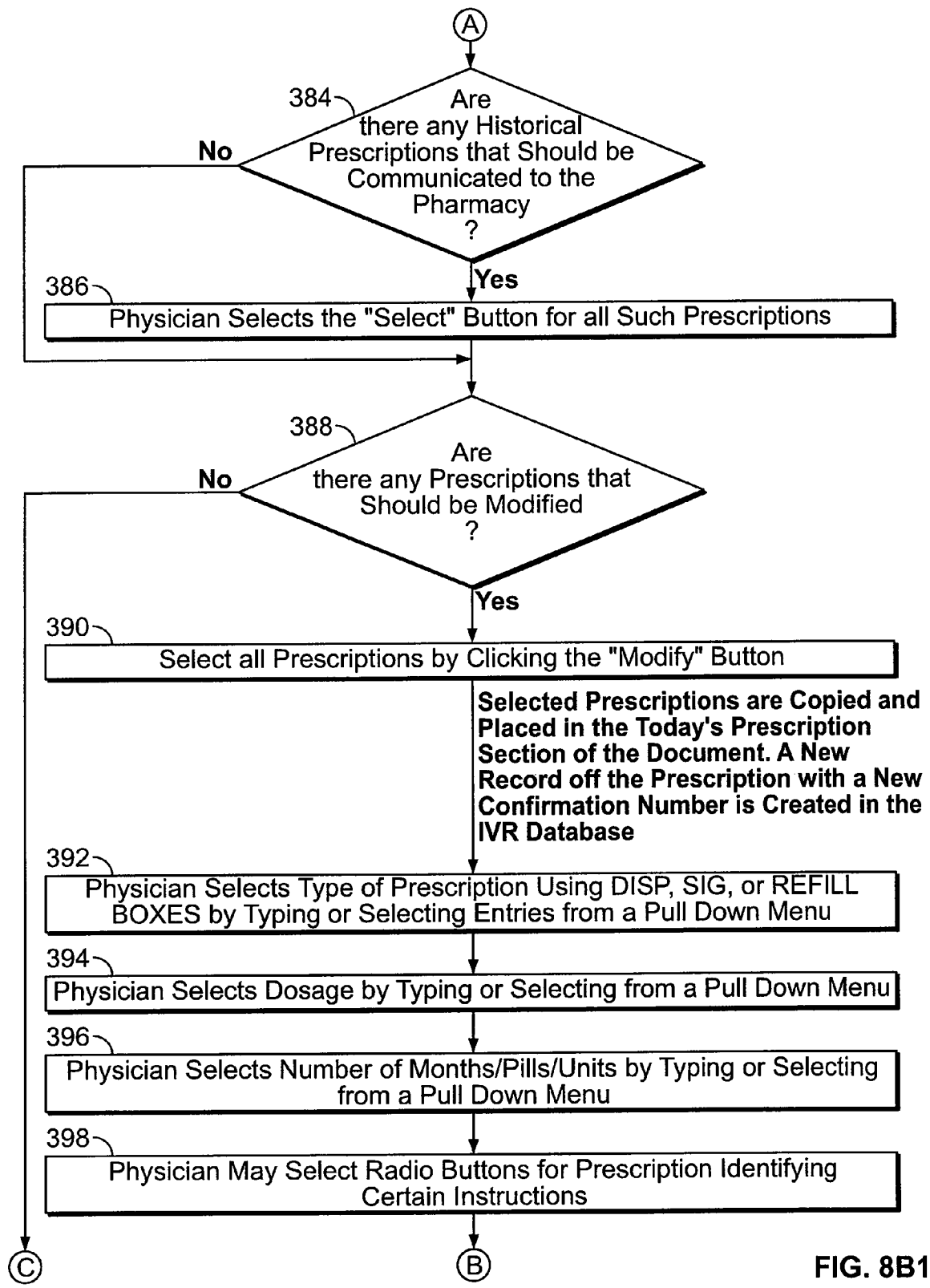
FIG. 8B1

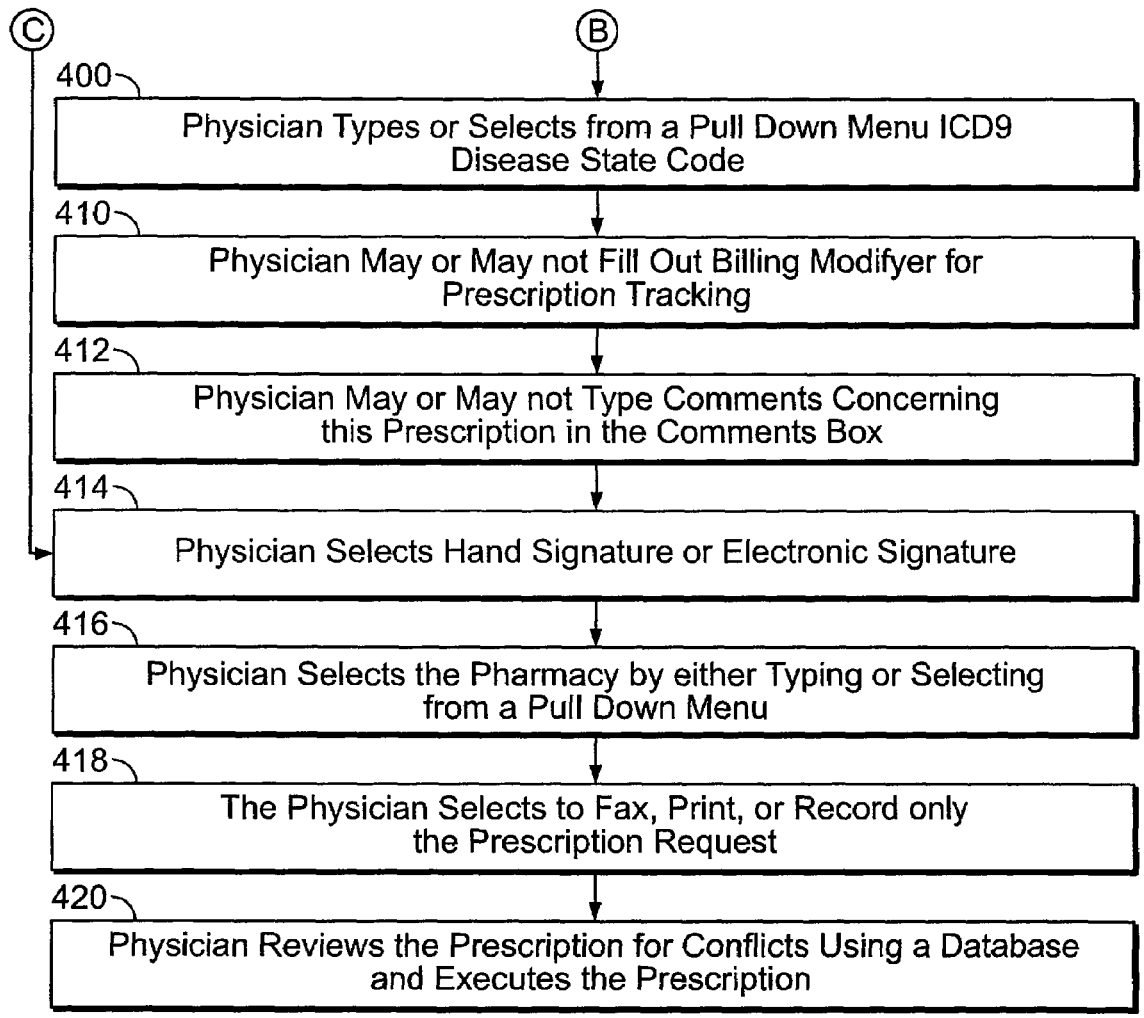
FIG. 8B2

Triage Automated IVR

Patient Report Requests (Details)

| Field | Value |
|---|---|
| Date | 2000/09/13 |
| Time | 10:29:11 |
| Report Type | EKG |
| Destination Type | Doctor's Office |
| Destination Name | CARDIAC STUDY CENTER |
| Phone Number | 2535727320 |
| Fax Number | 2536270712 |
| Patient Name | BASHORE, THELMA |
| Social Security # | 305249199 |
| wp # | Null |

☑ Processed

[Print] [Done]

SYSTEM AND METHOD FOR AUTOMATED PRESCRIPTION MANAGEMENT

FIELD OF THE INVENTION

This invention relates to automated prescription administration, and more particularly, an automated prescription voice system accessible to a user via a conventional telephone using DTMF tones interconnected with databases using fax on demand and internet protocols.

BACKGROUND OF INVENTION

Hospitals and medical offices in the United States handle millions of requests for prescription refills a day from pharmacies seeking to meet patients needs. These requests are typically handled in one of the following three ways. The pharmacy may leave a voice mail message that is transcribed by hand. The prescription is then authorized by the physician and called back to the pharmacy over the telephone or transcribed again and faxed to the pharmacy. Alternately, the pharmacy faxes the prescription request to the physician's office and the physician approves the fax and faxes it back to the pharmacy. In many cases the fax is unclear and the physician's office must telephone the pharmacy for clarification. Finally, the pharmacy may send a written form over the internet, either through e-mail or as a completed form using a prescription generation service.

Each of the above methods suffers from disadvantages. Listening to voice mail prescription requests and transcribing these requests is time consuming and expensive. Additionally, there are 89,000 unique prescriptions available for dispensing in the U.S. today, many of them with similar sounding names. For example, Celebrex is an arthritis drug, Cerebyx is a seizure drug and Celexa is an antidepressant, each of which has been mistaken for the other in clinical settings. Voice systems, which rely on transcribing information by hand, create the opportunity for physicians to make prescription errors. Faxed prescription requests are often hard to read because of poor transmission quality. Electronic communication of prescription requests is the most accurate, but with many physician's in the US not having computers in their office, the penetration of this technology is low. Also, physicians and pharmacies do not communicate about drugs in the same manner. Pharmacies use a numerical identification and physicians almost exclusively use brand marketing or generic nomenclature. The available systems that deal with prescription requests allow the pharmacy to identify the patient from a preexisting database and then record a voice message defining the drug and dosage being requested.

Current Interactive Voice Response (IVR) systems allow users to call a specified telephone number and, using DTMF tones or the human voice, navigate a menu to various application modules (i.e. services). These automated systems provide voice messages to a user over a telephone line and process the user's tone type telephone key presses (DTMF tones) as input. The messages played by the system can be tape recorded human voice messages or machine generated speech. These systems answer the telephone call and begin interacting with the user automatically.

IVR systems may require the entry of an account number, customer number, or password before access to the application modules is allowed. Once in the module, the messages from the system can provide the user with information, prompt the user to enter data or make a selection from a variety of choices. For example, a message can state: "For choice A, press one; For choice B, press two; For choice C, press three." If the number of choices is large, it may be necessary to present the choices in more than one menu. In that case, the final part of the message would prompt the user to provide a particular input in order to receive an additional message that lists other choices (i.e., "Press nine to hear more options").

The user navigates through the system by providing appropriate input at each message to get to the next desired message or to activate a desired option. The user may gain access to information stored in one of the many databases. This information may be communicated using recorded human voice messages or machine generated speech. The user may also be allowed to take action based on a provided service. For example, a user may activate a newly issued credit card by entering personal identification information and card information. The user may also be able to enter information into the system either by using their voice to create a recording or by using their voice to cause the system to recognize words and their preprogrammed action. The user may also enter information using the tones generated on the telephone keypad. For example, a voice query may ask the user to input their telephone number using the keys on the telephone. In this case the user may have already identified himself by the use of a particular account name or personal identification number. The system may create a record of the identity of the user from a preprogrammed database and add to that record information that the user enters or selects, such as their telephone number.

Prior art allows for the selection of options to add to the newly created record from a pre-existing database. Though the creation of a database record is possible, most IVR systems are designed to provide information to users, or to allow users to take some action such as credit card activation. Most systems are not designed to create database records as their primary function.

A database is a set of information characteristics about a unique subject. Database tables are often stored in database programs on computer hard disks. IVR systems can be made to create records in database tables if these databases reside on computers with an IVR interface. In the table below, the database captures certain demographic information about the subject parties.

TABLE 1

| Last name | First Name | Date of Birth | Social Security | Patient Number |
|---|---|---|---|---|
| Fox | Tom | Feb. 4, 1038 | 476-32-9374 | Franklin |
| Wilkins | Maria | Dec. 23, 1954 | 559-93-2836 | Simms |
| Anderson | Julie | Jul. 15, 1972 | 020-68-0022 | Hardgrove |

The information can be sorted in many ways. For example, the database may be made to display all subjects who were born in a particular year or who have a particular first name. This stored information can be linked in relational databases. A relational database is a database that has the ability to link two or more database tables together using unique characteristics or keys.

Prior systems, however, do not adequately create an interactive relational database that captures specific information to make a medical decision regarding prescription drug use and, once the decision is made, execute the planned action of that decision. Prior art does not allow for the consolidation of this information into a database about specific patients for transmission to healthcare providers over fax and internet protocols. Additionally, the prior art does not provide the service of consolidating a patient's full range of active prescription drug regime that is bid out to various commercial entities using internet protocols.

Accordingly, it is an object of this invention to provide an interactive voice response system that allows for absolute identification of drug and dosage information.

It is another object of this invention to provide a system that links patient identification to a specific medical record held by the physician and creates a patient prescription history database.

It is another object of this invention to provide a system that makes databases available to practitioners using fax on demand and internet protocols.

SUMMARY OF THE INVENTION

The present invention is directed to a system of creating a database based on prescription drug refill requests that are free from incorrect prescription drug identification and incorrect patient identification. The system reduces the time required to process such requests and creates a patient drug history that is accessible to "fax on demand" and internet protocols.

Removing the hand written transcription component of the prescription drug request process allows for the exact identification of prescription medication using a universally accepted 13 digit unique identifier. There are approximately 89,000 prescriptions available in the United States. Many of these drugs have similar names. The invention allows for the exact identification of the drug based on the 13 digit unique identifier called an NDC number. All drugs available for dispense in the United States are issued an NDC number which stipulates the drug name, dosage and delivery method (solid or liquid) by the FDA.

The invention creates a database entry of the prescription request and asks the pharmacist to identify the desired medication by keying in the 13 digit NDC number. This NDC number is then confirmed by the invention, which speaks the commercial name to the pharmacist and asks for approval of the drug and dosage. The invention creates 3 safety checks for correct identification of the drug. NDC numbers are typically not known and not used by physicians. Physicians typically use a drug's commercial or generic name. The invention causes a database entry to be created for each request that lists the NDC number as well as the commercial name and dosage of the requested drug. This information is then displayed to the processing physician. The physician who is processing this request does not have to guess as to the true name or dosage of the request. The invention generates a database prescription refill request that has a verified unique NDC number as well as the unique nomenclature and dosage.

Additionally, the exact identification of the desired patient may be based on a social security number, patient name or date of birth. Similar to errors generated for incorrectly transcribed prescription drugs, confusion over which patient is requesting the prescription refill request currently exist. A physician's staff or pharmacy may incorrectly identify a patient by shortening a name, for example, from Robert to Bob, or omitting a middle initial on a faxed request or voice mail transcription. The consequences are often as disastrous as prescribing an incorrect drug. The system solves this problem by forcing the pharmacist to identify a patient based on unique information generated from the patient's medical record stored at the physician's office. This unique identifier is linked to the internal record number used by the physician's office for the patient's chart. In cases where identity and diagnosis information is required to ensure that the correct patient is approved for appropriate medication the chart or electronic medical record can be pulled to immediately determine if the refill request is appropriate. The invention virtually eliminates the possibility for incorrect prescriptions caused by transcription errors or illegible faxes.

The invention generates a unique tracking number for each prescription refill request that records all data provided by the pharmacy, the user who authorized the refilled prescription, and the date and time the prescription was authorized for refill. The invention drastically reduces the time required to process a prescription refill request. The invention improves on current practice by forcing the pharmacy to select a patient from a patient database that correctly matches that patient to a medical record that contains the patient's prescription history.

Further, the invention allows the refill of prescriptions to be completed at any location with a computer terminal. Because the invention is stored on a computer hard disk that may be shared over a network or the internet, a prescription refill request may be answered from any location accessible to a wire or wireless communication source. The invention also allows physicians to access a patients drug history. This makes it possible for emergency room physicians who are treating a patient to call a specified number, enter a unique pin number, identify the patient and have the prescription history faxed or e-mailed to their location immediately. This results in better medical decisions making at a time crucial to the care of a patient.

Furthermore, the invention allows for the sorting of approved prescription refill requests. This allows physicians to identify patients who have been given drugs that are being recalled, identify patients who may benefit from new drugs recently approved or identify patients who may qualify for clinical trials for new therapy. This also allows physicians to identify patients with classified disease states as stipulated by ICD-9 codes. This allows administrators to evaluate the plan of treatment for specific disease states.

The invention allows for the consolidation of all ongoing medication into a single Super Prescription request and allows for the bidding out of that Super Prescription request to commercial entities. Patients are often prescribed single drug prescriptions for varying lengths of time by potentially different physicians. The invention automatically captures all prescription refill requests from pharmacies when they telephone into the system or access it using internet protocols into a single database. The invention also captures new prescription information automatically when a physician writes a prescription during a patient visit. Additionally, the invention has a method for entering prescriptions issued by other physicians who may have seen the patient and prescribed medication. The result is a prescription database for a patient that includes all active medications, all discontinued medications and all drugs that the patient is allergic to or intolerant to.

The database can be made to produce a "Super Prescription" that displays all active medications that is electronically approved by the primary care physician for a uniform period of time, typically until the next patient visit. The prescription can then be sent electronically to all subscribing pharmacies for the lowest cost bid on the full super prescription. The result is that the patient gets the lowest price on a complete medication package without having to shop individually for each prescription. The patient also does not have to worry about a single prescription expiring before their next regularly scheduled visit, as all prescriptions will be made to expire at the same time. The physician provides better and more complete care for the patient by ensuring that the patient's treatment regime of pharmaceuticals is not interrupted. This process also reduces the number of individual prescription refill requests the physician must process between visits, reducing the physician's workload by approximately 30 minutes per day.

The following detailed description of embodiments of the invention, taken in conjunction with the appended claims and accompanying drawings, provide a more complete understanding of the nature and scope of the invention.

BRIEF DESCRIPTION OF DRAWINGS

FIGS. 3A and 3B are flow diagrams illustrating the process for creating a prescription refill request of the present invention.

FIGS. 5A and 5B are flow diagrams illustrating the process of creating prescription history requests of the present invention.

FIGS. 8A and 8B are flow diagrams illustrating the process of creating new prescriptions and "Super Prescriptions".

FIG. 11 is a computer screen image of the Prescription Refill Request.

FIG. 13 is a computer screen image of the Prescription Generator.

DETAILED DESCRIPTION OF THE PREFERRED EMBODIMENT

Figure 1:
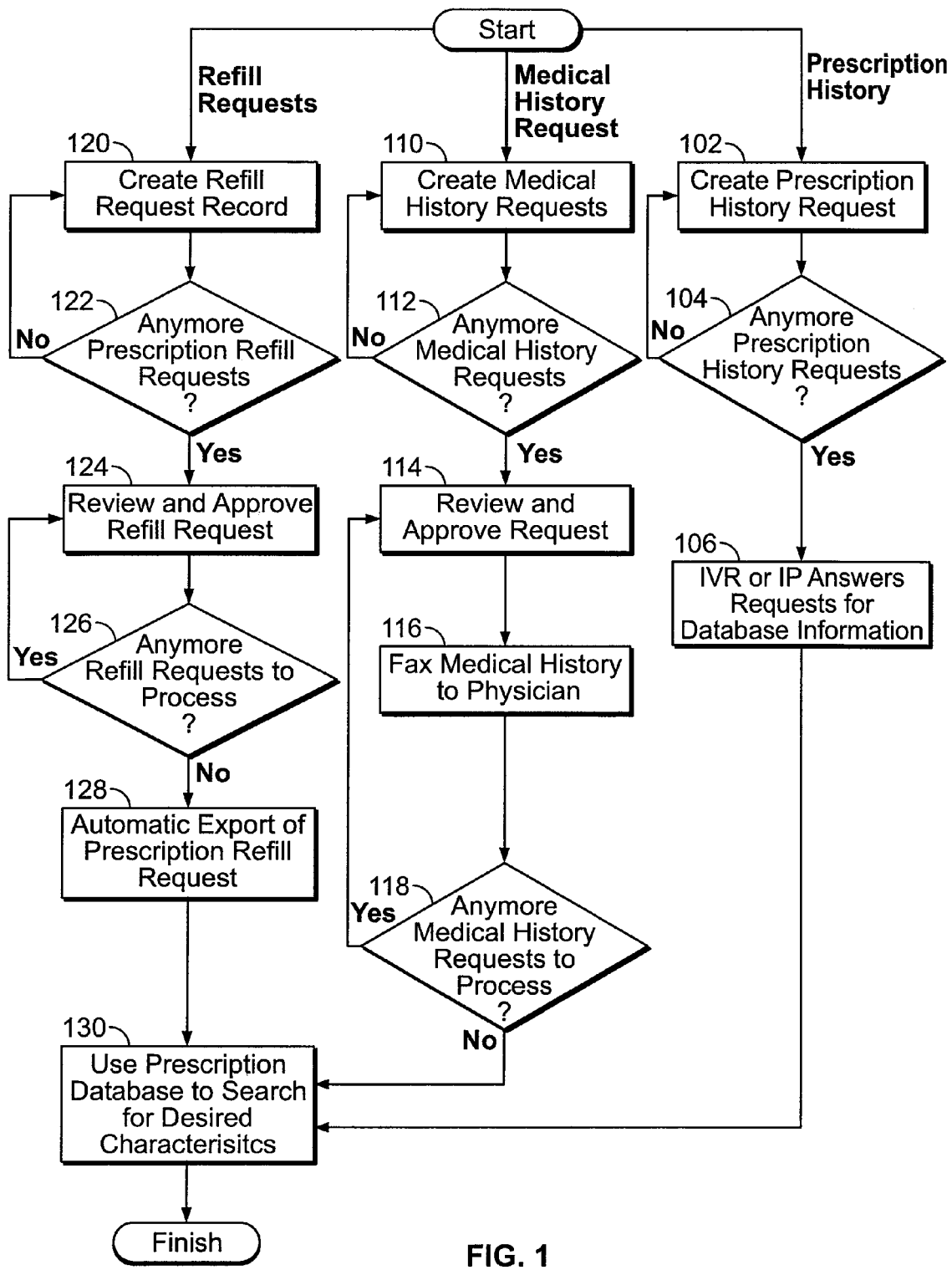
FIG. 1 illustrates an interactive voice response system according to the present invention
Figure 6:
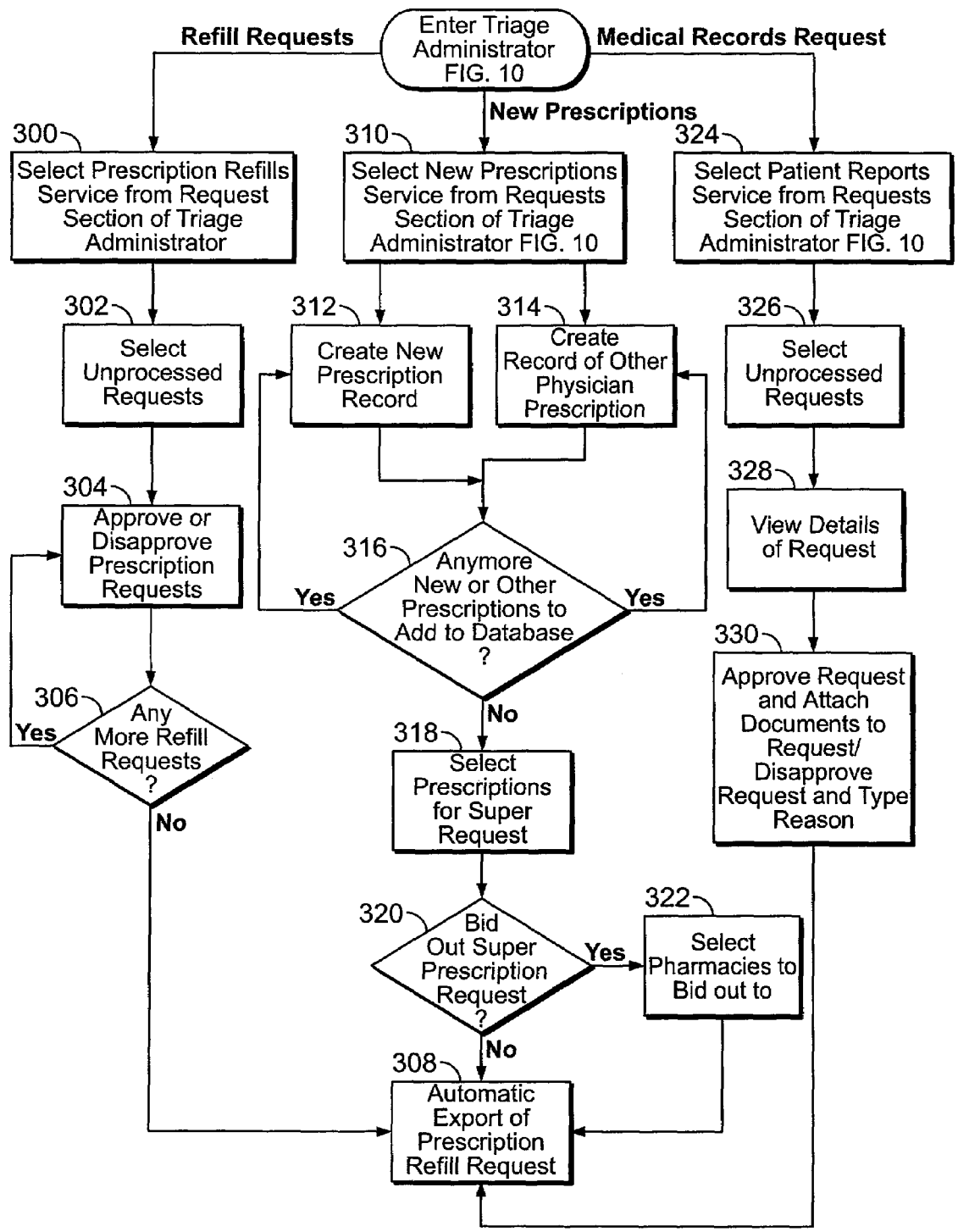
FIG. 6 is a flow diagram illustrating processing of all requests using the Triage Administrator.

FIG. 1 illustrates the interactive voice response (IVR) system of the present invention that is connected to the Triage Administrator network database (FIG. 6). The IVR system detects incoming telephone calls, answers the telephone call and provides the caller with various voice prompts. The IVR system accepts and processes input provided by the caller. The user provides input by pressing buttons on a DTMF telephone during the call. The IVR system allows the user to access a menu where the user is presented with three options for using the system. In the first option 120, the user depresses the "1" key if he is a pharmacy desiring to create a prescription refill request. In the second option 110, the user depresses the "2" key if he is calling from another healthcare entity and desires to create a patient medical history request. In the third option 102, the user depresses the "3" key if he is a healthcare professional desiring a prescription history for a patient.

Option 120 allows the user to create a prescription refill request. Step 122 presents the option of creating another prescription refill request for the same or a different patient. Step 124 allows the physician to review the refill request and approve or disapprove the request. In step 126 the physician completes any additional refill requests. In step 128 the refill request is either faxed or e-mailed to the requesting pharmacy. In step 130 the physician may use database analysis techniques to search the resulting database for records that meet the desired characteristics.

In option 110 another healthcare entity such as a clinic, hospital or nursing home may call the system and create a request for the medical history for a patient. In step 112 the system allows the caller to make additional medical history requests for different patients. In step 114 the physician reviews the request and electronically attaches a patient's medical history to the request. In step 116 the request and medical history are faxed or e-mailed to the requesting organization. In step 118 additional medical history requests are processed. In step 130 the physician may use database analysis techniques to search the resulting database for records that meet the desired characteristics.

In option 102 a physician or healthcare professional requests immediate information concerning a patient's prescription history. In step 104 the physician may request the same information for additional patients. In step 106 the system either faxes or e-mails the requested prescription history information to the desired fax number or e-mail address. In step 130 the physician may use database analysis techniques to search the resulting database for records that meet the desired characteristics.

Figure 2:
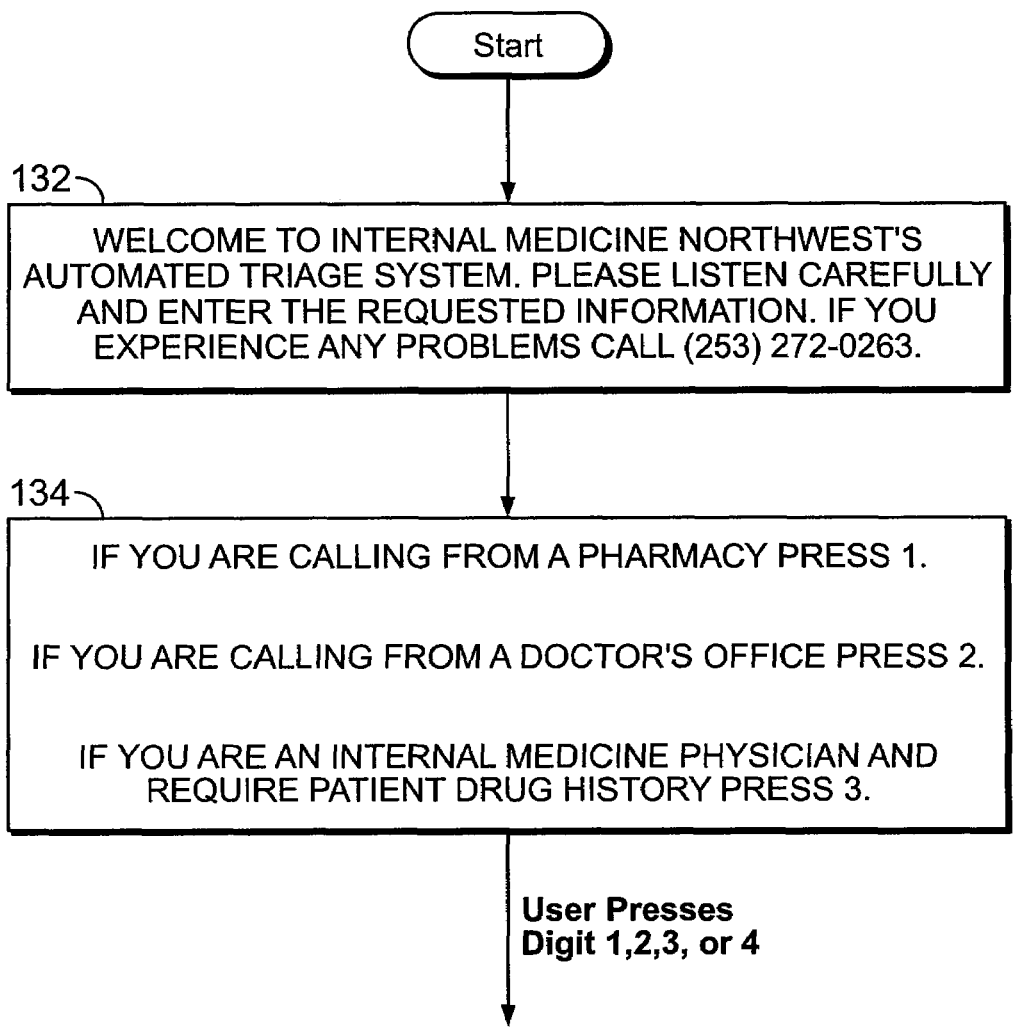
FIG. 2 is a flow diagram illustrating the processing when a telephone call is first received by the interactive voice response system of the present invention.

FIG. 2 refers to the opening menu that the caller hears when his call is answered by the system. In step 132 the caller hears a general greeting. In step 134 the caller is prompted to select the type of organization he represents, a pharmacy, a doctor's office or an internal medicine physician. The system then presents options to meet that type of organization's informational needs.

FIG. 3A and FIG. 3B illustrate the process the pharmacy goes through to enter a prescription refill request. In order for a complete prescription refill request to be created and a confirmation number to be generated, the system must positively establish the pharmacy's identity, the patients' identity, the drug identity, the prescribing physician and the date of the last refill. The caller must confirm each piece of information by taking an action such as depressing a key on the telephone keypad. This is necessary to ensure that prescription requests are only issued for the correct medications to the correct patients.

In step 140 the system compares the identification information provided by a caller to a database of stored pharmacy names and telephone numbers. If the telephone number is recognized, the system bypasses the general greeting in step 132 (FIG. 2) and asks the caller to confirm their identity in step 144. If the caller identification information is not recognized, the caller is transferred to the general greeting in step 132 (FIG. 2). Once the caller depresses the "1" key to indicate they are a pharmacy in step 134 (FIG. 2), they are transferred into the Pharmacy service and asked to enter their phone number in step 142. The system compares the entered phone number to a database of all pharmacy phone numbers. The system speaks the pharmacy name to the caller in step 144 and asks the caller to confirm their identity. If the caller depresses the "2" button to deny his spoken identity, he then has to re-enter his telephone number in step 152. If the caller denies his spoken identity for a second time, the system tells the pharmacy that they are not listed in the pharmacy database and terminates the call.

If the caller confirms their identity by depressing the "1" key in step 154 or in step 144, then he moves onto step 146 where the system asks the caller to begin to identify the patient by typing in the first three letters of the patient's last name. Next, in step 148, the system asks the caller to type in the patient's date of birth. This information is unique to every patient and can be used by the system to positively establish a patient's identity. In step 150, the system compares this information to a database of all patients and speaks the patient's name to the caller. The caller presses "1" to confirm the patient's identity or "2" to deny the patient's spoken identity. If the caller denies the patients spoken identity, the caller is asked to enter the patient's social security number in step 158. The social security number is unique to every patient and can be used by the system to establish identity. The caller presses "1" to confirm the patients identity or "2" to deny the patient's spoken identity. If the caller denies the patient's spoken identity for a second time (step 160), the system tells the caller that the patient is not listed in the patient database and terminates the call (step 162).

If the caller accepts the patient identity in step 150, he is asked to enter the 13 digit NDC number of the medication for which he requires a prescription (step 164). In step 166 the caller is asked to confirm the drug's spoken identity. If the caller denies the drug's spoken identity by pressing the "2" key in step 166, he is asked to reenter the drugs 13 digit NDC number in step 168. In step 170 the caller is again asked to confirm the spoken name of the drug. If the caller denies the spoken identity of the drug for a second time, the system tells the caller that the drug cannot be identified and terminates the call (step 172).

If the drug's identity was confirmed in step 166 or in step 170, the system asks the caller to enter the date the prescription was last filled in step 174. In step 176 the system asks the caller to confirm the spoken date of the last refill date. If the caller denies the date spoken by depressing the "2" key, the caller is then asked to enter the last refill date again in step 182. The caller is then prompted to confirm the spoken date of the last refill. If the caller denies the spoken date of the last refill, he is placed in a "do-loop" where he is continually asked to enter and confirm the last refill date until he confirms the data. If the caller presses "1" in step 176 or in step 184 and confirms the date of the last refill, he is asked to enter the initials of the prescribing physician in step 178. In step 180 the caller is asked to confirm the spoken identity of the prescribing physician. If the caller denies the spoken name of the prescribing physician and depresses the "2" key, he is asked to enter the prescribing physician's initials again in step 190. If the caller again denies the spoken identity of the prescribing physician for the second time in step 192, the system tells the caller that the prescribing physician will try to be identified in step 194. The caller is then transferred to step 186.

If the caller had depressed the "1" key and confirmed the identity of the prescribing physician in steps 180 or 192, the caller progresses to step 186 where the caller is asked to enter the quantity of medication desired. In step 188, the system then asks the caller to confirm the spoken quantity of medication desired. If the caller denies the spoken quantity of medication desired by depressing the "2" key, the caller is asked to enter the desired quantity again in step 200. If the caller again denies the spoken quantity in step 202, the caller is placed in a "do-loop" until the correct quantity is entered and confirmed in steps 200 and 202. If the caller confirms the spoken quantity of medication desired in step 188 or 202, the caller is asked to confirm the spoken name of the patient, the spoken name of the medication and the quantity desired in step 196. If the caller denies the spoken patient, medication or quantity, the call will be terminated in step 204. If the spoken identity of the drug and the spoken quantity of medication is confirmed, the system issues an unique confirmation number signaling a successful request and asks the pharmacy if there are anymore requests to enter. If there are no more requests, the call is terminated.

Figure 4A:
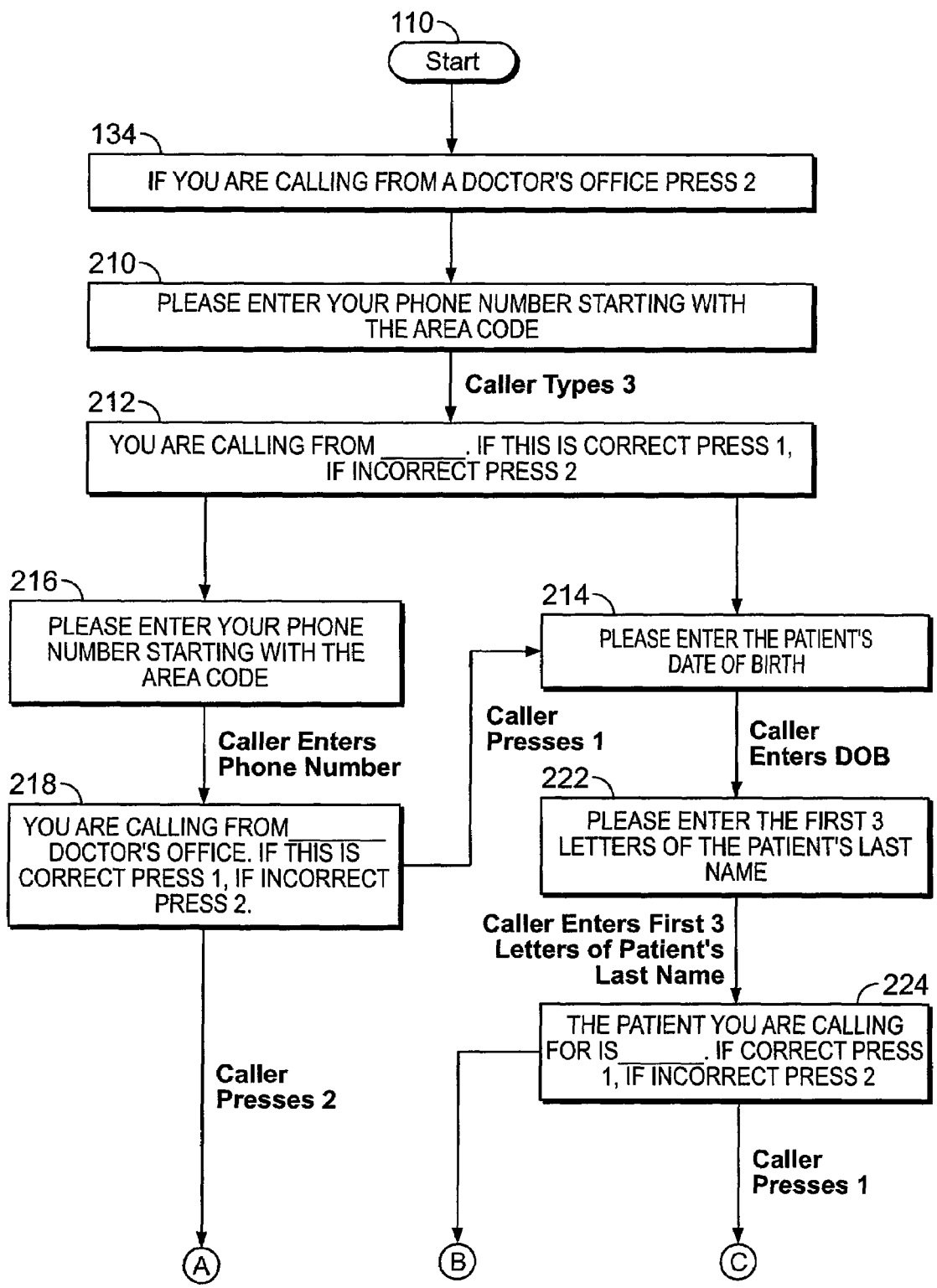
FIG. 4 is a flow diagram illustrating the process for creating a medical history request of the present invention.
Figure 4B:
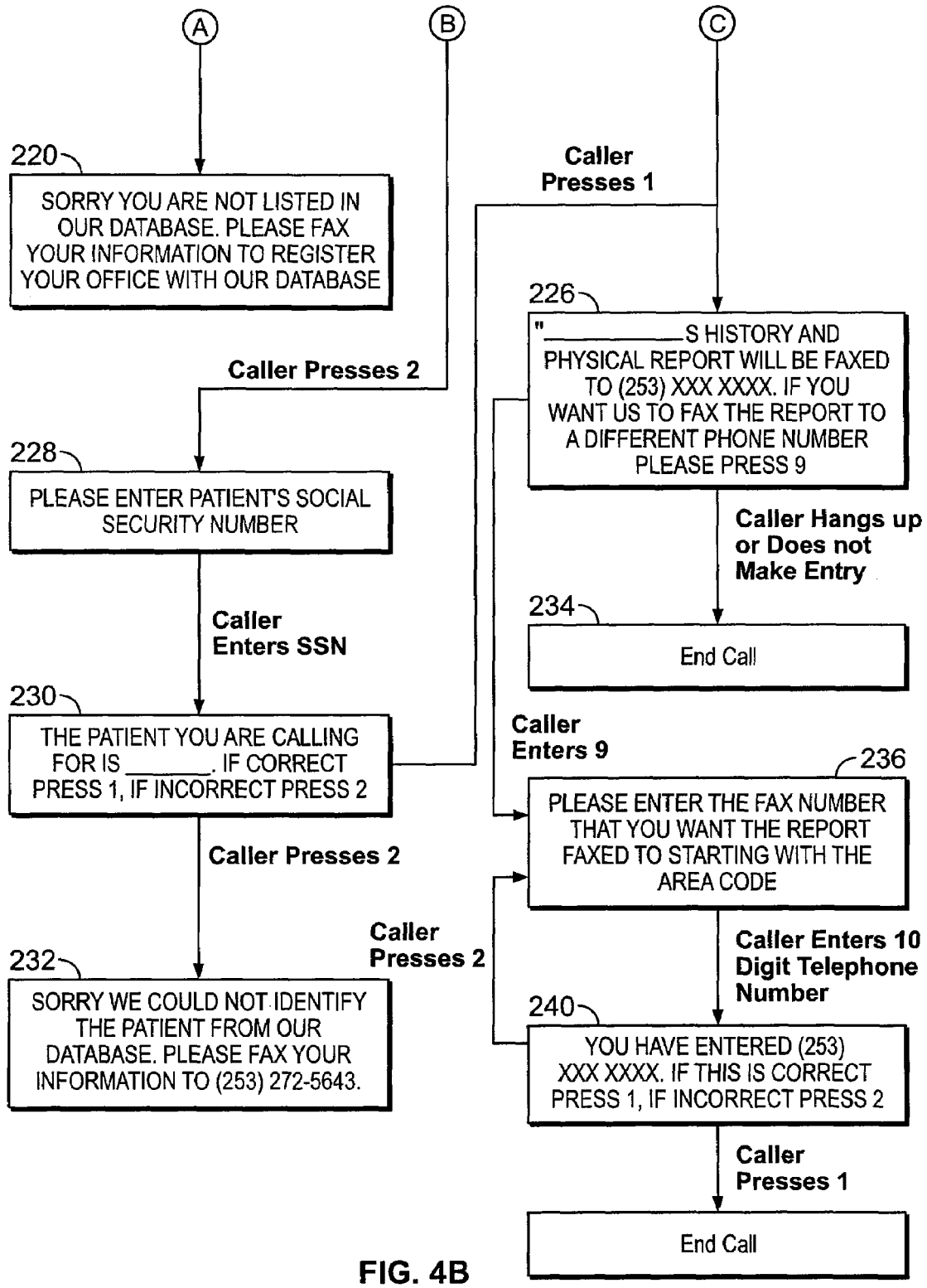

FIG. 4 refers to the option defined in step 110 (FIG. 1) that allows a healthcare entity to call the system and generate a request for a patient's medical history. In order to complete a request, the system must positively establish the correct identity of the healthcare entity, the identity of the patient whose medical records are being requested and the delivery address, fax number or e-mail address where the information will be sent. The caller must confirm each piece of information by taking an action such as depressing a key on the telephone keypad.

In step 132 of FIG. 2, the caller is greeted with the opening menu of the system. In step 134 of FIG. 2 he is asked to identify the type of entity he is calling from. If the caller selects Doctors office by depressing the "2" key (FIG. 4), the system asks the caller to enter his telephone number in step 210. The system matches the entered telephone number to a pre-existing database and speaks the doctor's office name to the caller in step 212. The caller accepts the spoken identity of the doctor's office by pressing "1" or denies the spoken identity of the doctor's office by pressing "2". If the caller denies the spoken identity, he is asked to re-enter his telephone number in step 216. The caller is again asked to confirm the doctor's office spoken identity in step 218. If the caller denies the doctor's office spoken identity for the second time by pressing "2", the system indicates that the doctor's office is not in the system's database and terminates the call.

If the caller confirms the doctor's office spoken identity in step 218 or in step 212 the system moves forward to identify the patient. In step 214 the caller is asked to enter the patient's date of birth. Next, in step 222 the caller is asked to enter the first three letters of the patients last name. The system then speaks the patient's name to the caller in step 224. The caller confirms the patient's identity by pressing the "1" key or denies the patient's spoken identity by pressing the "2" key. If the caller denies the patient's spoken identity by pressing the "2" key, the caller is asked to enter the patient's social security number in step 228. The system then speaks the patient's name in step 230. The caller confirms the patient's identity by pressing the "1" key or denies the patient's spoken identity by pressing the "2" key. If the "2" key is selected for the second time, the system indicates that the patient is not in the database and disconnects the call.

If the caller accepts the patient's spoken identity in either step 230 or step 224, the system indicates that the requested information will be faxed to the caller's fax number and speaks that fax number in step 226. In step 226 the system also allows the caller to request a different number to fax the requested information to by depressing the "9" key. The system disconnects the call if the "9" is not depressed in step 234. If the "9" key was depressed in step 226, the system asks the caller to enter a new fax number in step 236. The system then speaks the new fax number back to the caller in step 240. If the caller confirms the new fax number by depressing the "1" key. The call is then terminated. However, if the caller denies the new spoken fax number, the caller is asked to enter the new fax number again. The caller remains in this loop until he accepts a spoken fax number.

Figure 5B:
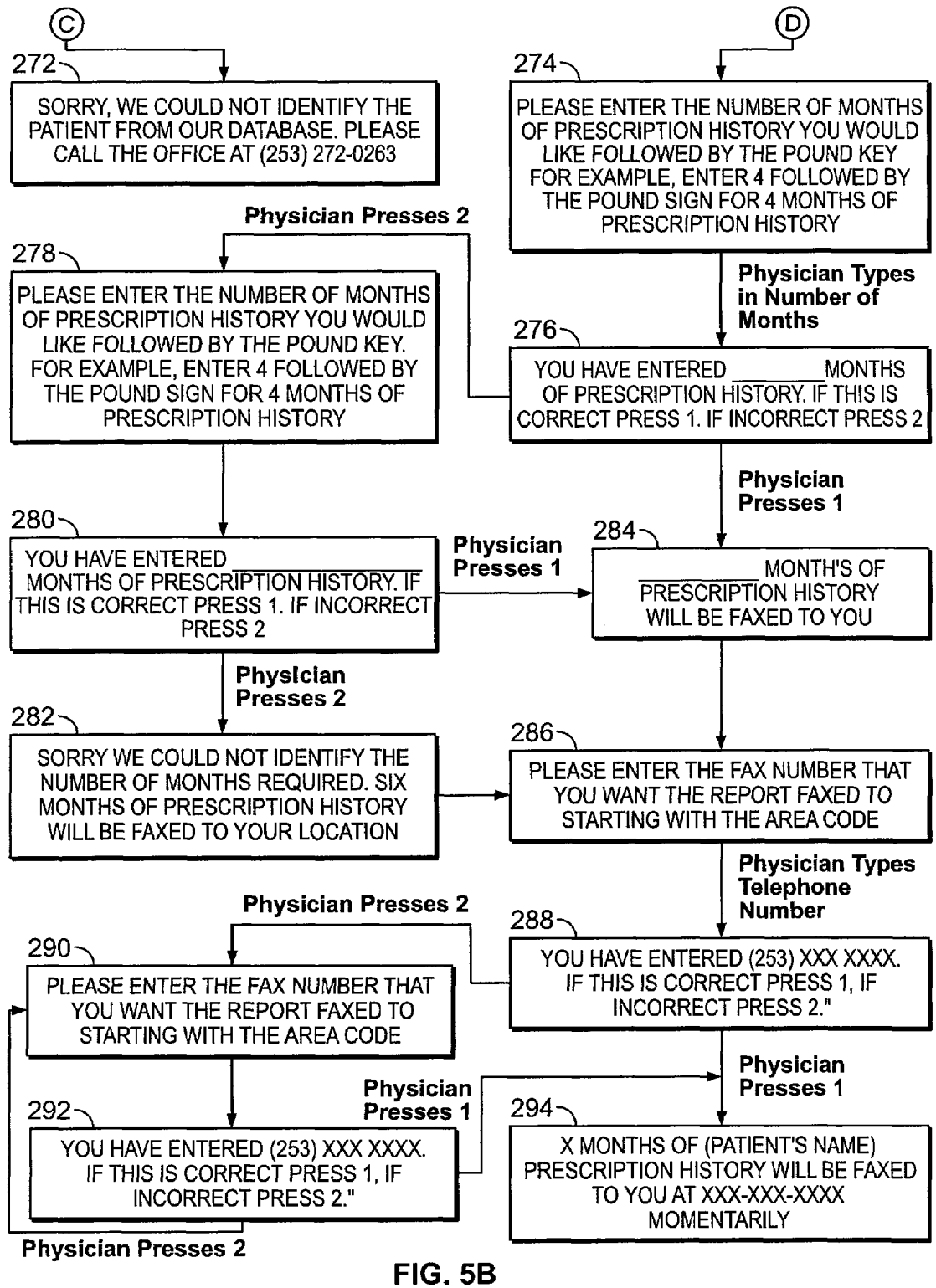

FIG. 5A and FIG. 5B refer to the process an affiliated physician goes through to have a patient's prescription drug history immediately sent to him. Unlike the services detailed in FIGS. 3A and 3B and FIG. 4, the service described in FIGS. 5A and 5B is automatic. This service is designed to meet the needs of emergency room physician's for accurate prescription drug history information. The emergency room physician calls the system and identifies the patient and the fax number or e-mail address where he wants the information sent. Assuming the physician enters a valid username and password, the system will fax or email the requested information immediately.

The caller indicates that he desires a patient's prescription drug history by depressing the "3" key at the main menu in step 134 of FIG. 2. The system then prompts the physician to enter his user identification in step 242 (FIG. 5A). The system asks the physician to enter his security password in step 244. The system compares the information to a pre-existing database of authorized users to determine the identity of the caller. If no match is found, the physician is asked to enter his user identification again in step 246 followed by his security password in step 248. If no match is found the second time the call is terminated.

If a match was found in step 244 or in step 248 the system speaks the physician's name in step 252. In step 254 the system asks the physician whether he wants to identify the patient using last name and date of birth or by social security number. If the physician selects social security number by depressing the "2" key, he is asked to enter the patient's social security number in step 264. If the physician selects last name and date of birth by depressing the "1" key, the system asks him to enter the patient's 4 digit year of birth in step 256. Next, the system asks the physician to enter the patients two digit month of birth in step 258, followed by the patients two digit date of birth in step 260. The physician is prompted to enter the first three letters of the patient's last name in step 262. The system then speaks the patient's identity in step 266. The physician confirms the patient's spoken identity by depressing the "1" key or denies the patient's spoken identity by depressing the "2" key. If the "2" key is depressed, the system determines if this is the first denial of the patient's spoken identity in step 268. If it is the second denial, the system denies access and terminates the call in step 272. If it is the first denial, the system asks the caller if he would like to identify the patient using social security number or using last name and date of birth in step 270. If the physician chooses last name and date of birth by depressing the "1" key, he is transferred back to step 256 and he enters the patient information as before. If the physician chooses to identify the patient using social security number by depressing the "2" key, then he is transferred back to step 264 and he enters the patient information as before.

If the physician confirms the patient's spoken identity in step 266, the system prompts the physician to enter the number of months of the patient's prescription history in step 274 (FIG. 5B). The system speaks the number of months entered and asks the physician to confirm that this is correct. If the physician denies the spoken number of months then the system prompts him to enter a number of months again in step 278. In step 280 the physician is asked to confirm the number of months entered. If the physician denies the spoken number of months for the second time, then the system defaults to 6 months in step 282. If the physician confirms the number of months then the system speaks in either step 280 or in step 276, the system tells the physician that the information will be faxed to him in step 282.

The fax system is a default setting that can be substituted with an e-mail address generated from a database. In step 286 the system asks the physician to enter the fax number that he wants the information sent to. The system then speaks the fax number in step 288. The physician confirms the spoken fax number by depressing the "1" key. The system then tells him that X number of months will be faxed to the number he entered. If the physician denies the spoken fax number, he is asked to re-enter it in step 290. The system speaks the re-entered number in step 292. The physician confirms the spoken fax number by depressing the "1" key. The system then tells him that X number of months will be faxed to the number he entered. If the physician denies the fax number by depressing the "2" key, he is transferred back to step 288. The physician remains in this loop until he confirms the fax number.

The above Figures referred to the Interactive Voice Response system that enabled callers to create requests using the present invention, the following Figures detail the user interfaces that allow the hosting physician to process requests and create new prescriptions. FIG. 6 refers to the user interface for the system, known as the Triage Administrator and visually depicted in FIG. 10. In step 300, the physician enter the Triage Administrator and select the Prescription Refills button. All prescription refills are displayed. The user then selects unprocessed requests in step 302. The physician views the information contained in the refill request, visually depicted in FIG. 11, and approves or disapproves the request for refill in step 304. The physician then determines if there are anymore requests in step 306 and processes them accordingly. Completed prescription requests are transmitted automatically in step 308 using fax or internet protocols.

In step 310 the physician selects the new prescription service from the Triage Administrator. The Physician uses this service in the exam rooms to generate new prescriptions in step 312 or to add prescriptions generated by other physicians to the database in step 314. The invention is capable of running from a networked computer or using a handheld device like a Palm VII, Motorola Timeport, or RIM's Interactive Pager 850. The physician determines if there are anymore prescription requests in step 316. If there are, he selects the type and continues in a do-loop until all prescriptions have been generated or entered.

In step 318 the physician selects active and historical medications to add to the current prescription in order to ensure that all medication is dispensed for a uniform time period. This consolidated prescription is known as a "Super Prescription" and it ensures that the patient stays on the regime until the next scheduled visit. The "Super Prescription" prevents the patient from running around after single prescriptions. Next, the physician asks the patient if they would like their "Super Prescription" bid out to pharmacies. In the bid process, the physician sends the "Super Prescription" to selected affiliated pharmacies. The pharmacies provide a broken down and cumulative price for the entire "Super Prescription," including the shipping cost and the delivery date. These bids are submitted to the patient as they exit the physician's office. The winning pharmacy, the pharmacy of the patients choosing, will automatically receive the completed "Super Prescription" using fax or internet protocols in step 308.

In step 324 the physician selects the Patient Reports service from the Triage Administrator to process requests for a patient's medical history from other health care entities. Once selected, the Patient Reports screen brings up all patient report requests. In step 326 the user selects the view unprocessed requests only button to view open requests. The user then selects individual requests in step 328. The visual representation of these requests can be viewed in FIG. 12. In step 330 the user attaches the requested document or medical history summary to the request and faxes the report to the requesting party in step 308. Alternatively, the request and attached information may be sent using internet protocols.

Figure 7:
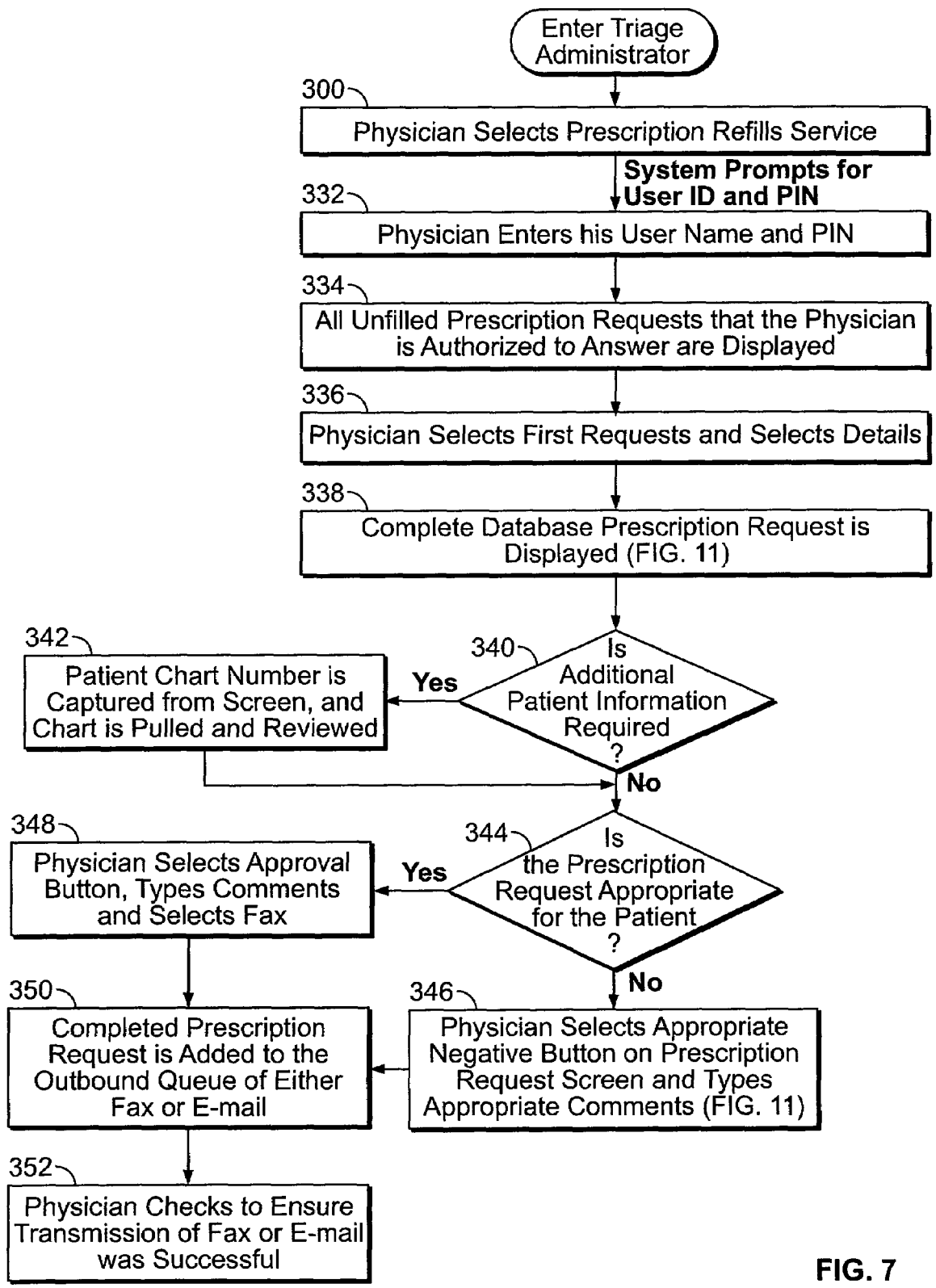
FIG. 7 is a flow diagram illustrating processing prescription refill requests.

FIG. 7 illustrates the actions taken when the user desires to process unfilled prescription refill requests. In step 300, the user selects the Prescription Refills button on the Triage Administrator (see FIG. 10). The user then types in his user name and Personal Identification Number (PIN) in step 332. In step 334 all unfilled prescription requests that the user has authorization to process are displayed on the screen. The user then selects the first uncompleted request and selects the detail button in step 336. The prescription refill request screen appears, illustrated in FIG. 11, displaying the request information in step 338. The user decides if additional information is required to process this request in step 340. If additional information is required, then the chart number is captured from the Prescription Refill Request screen and the chart is reviewed in step 342. If no additional information is required, the user determines if the refill request is appropriate for the patient in step 344. If the prescription refill request is not appropriate for the patient, the user selects the appropriate negative button on the Prescription Refill Request screen, illustrated in FIG. 11, in step 346. If the refill request is appropriate, the user selects the approved button and fills in any comments in step 348. The completed request is added to the outbound fax queue or to the outbound e-mail in step 350. The user checks to ensure that the request was sent in step 352.

Figure 8A:
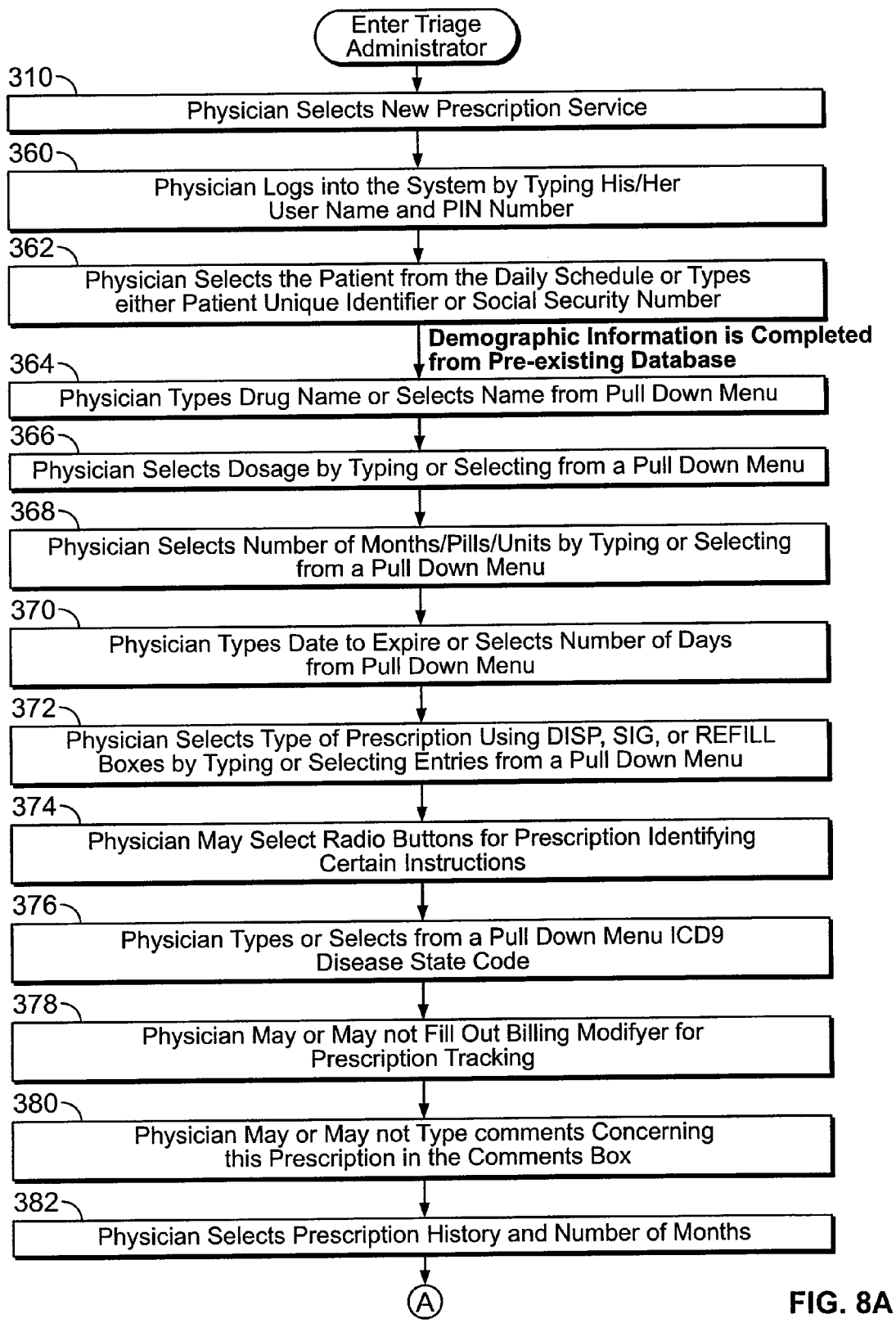

FIGS. 8A and 8B refer to the actions taken when the physician desires to generate a new prescription or enter a prescription generated by another physician. In step 310 the physician selects the New Prescription button on the Triage Administrator (see FIG. 10). The physician logs onto the system using a username and personal identification number (PIN) in step 360. The physician's name and title are automatically completed in the Medical Practitioner field of the Prescription Generator screen (see FIG. 13). In step 362, the physician selects the patient from the daily schedule or types either the Patient Unique Identifier number or the patient's Social Security Number. Once the patient is identified, all demographic information is populated in the patient section of the Prescription Generator (see FIG. 13).

The system identifies the drug using a pre-programmed database. In step 364 the physician types a drug name or portion of the drug name and a scroll down menu appears with close matches. The physician can continue to type with the scroll down menu eliminating incorrect choices and narrowing the list, or the user can scroll down and select the desired drug name. Next, the physician types or selects a dosage with the choices in solid or liquid form displayed on the screen in a pull down menu from a database table in step 366. In step 368 the physician types or selects the number of months the prescription is valid for, again from a drop down menu tied to a database table. In step 370 the physician may type an expiration date. The physician may also select and populate the DISP, SIG and REFILL boxes in step 372 to indicate specific instructions to the pharmacy. In step 374 the physician may also select buttons signifying certain instructions for the prescription. For example, the physician may select the following buttons: Discontinue, Allergic to, Intolerant to, Generic Substitution Permitted, Dispense as Written or May Substitute Formulary Equivalent with notification. In step 376 the physician populates the ICD9 disease state Code. The physician may or may not fill out the billing modifier in step 378. In step 380 the physician may type special comments in the comments field for the prescribed drug.

In step 382 the physician may select prescription history to view historical medication information. In step 384 (FIG. 8B), the physician may review some historical prescriptions, such as those that the patient is intolerant or allergic to, and select those prescriptions in step 386 to transmit to the pharmacy for informational purposes. In step 388 the physician decides if there are any historical prescriptions that should be added to the day's prescription to ensure that the patient has their full medication regime through their next visit. These prescriptions are selected in step 390 and placed, by the system, into the current days prescriptions with a record being produced in the system database. For these modified prescriptions, the physician selects the type of prescription in step 392 and the dosage in step 394. The physician selects the number of pills or units for the modified prescription in step 396. The physician may also select the Discontinue, Allergic to, Intolerant to, Generic Substitution Permitted, Dispense as Written, May Substitute Formulary Equivalent with Notification radio buttons in step 398 to specify filling information to the pharmacy. The physician may also complete the ICD9 disease state code in step 400 and the billing modifier in step 410. In step 412 the physician types any comments concerning this medication into the comments field.

The physician has now created a "Super Prescription" which is a prescription containing all current medications and any relevant historical medications. The physician selects hand or electronic signature in step 414 depending on whether the prescription will be printed, faxed or e-mailed. In step 416 the physician selects the pharmacy by typing it's name or selecting it using a drop down menu. In step 418 the physician selects the output method of fax, e-mail, print or for record. In step 420 the physician reviews the full "Super Prescription" for conflicts between drugs. The physician may use a preprogrammed database tied to the present system to screen for such conflicts. The physician then executes the prescription.

Figure 9:
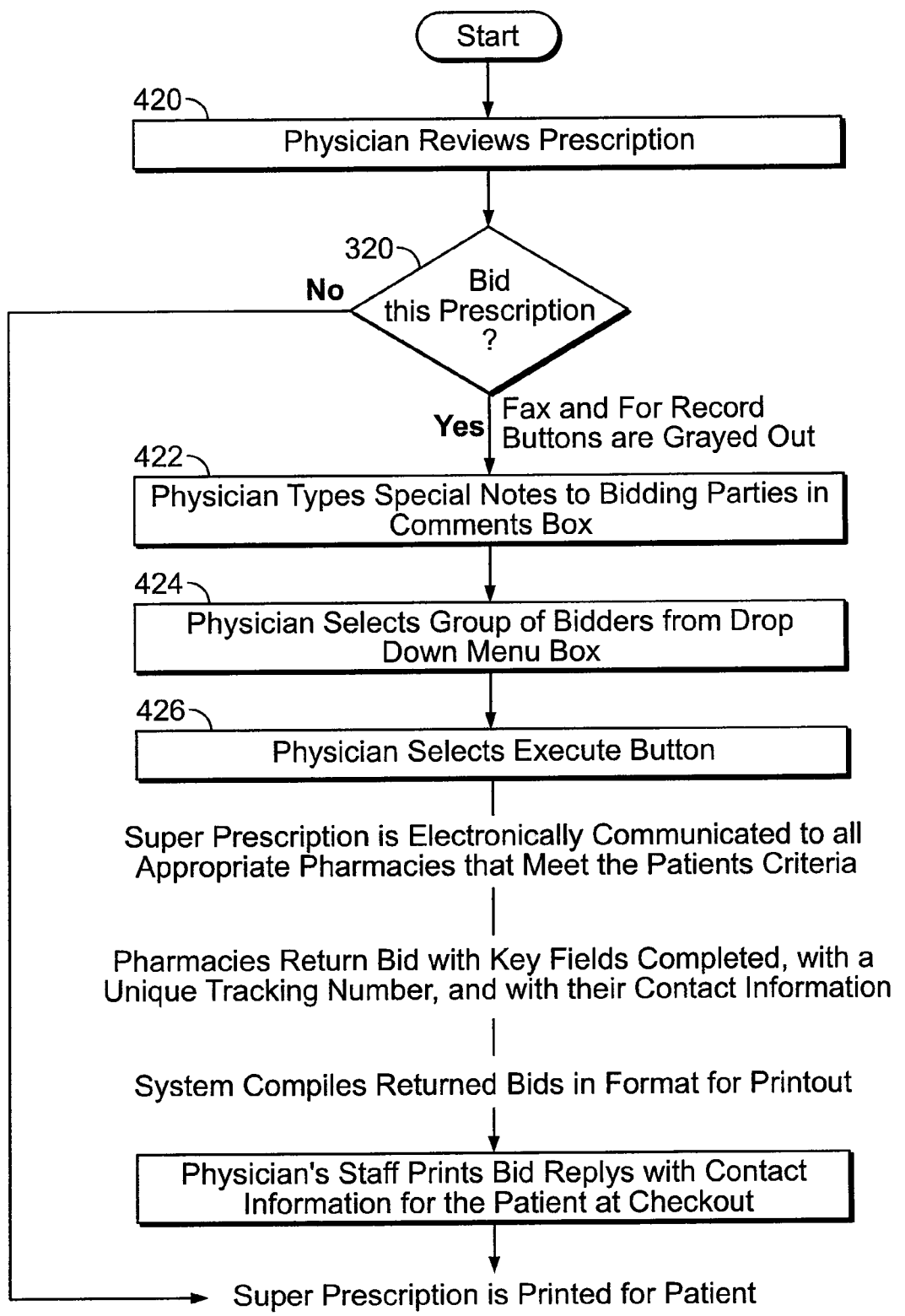
FIG. 9 is a flow diagram illustrating the process of bidding a Super Prescription.

FIG. 9 refers to the bid process for the "Super Prescription". The "Super Prescription" is a prescription issued by the physician that day including that day's medications as well as authorization for all current and relevant medications. After reviewing the "Super Prescription" for drug conflicts in step 420, the physician decides to bid out the prescription in step 320. When the bid out "Super Prescription" service is selected, the Fax and For Record boxes are grayed out and inactive (see FIG. 13). In step 422 the physician types special notes to the bidding parties. In step 424 the physician selects the type of subscribing pharmacies based on the patients request. For example, some choices are "local pharmacies only," "US pharmacies only," or "pharmacies with free delivery only." Once the type of pharmacy is selected, the physician selects the execute button in step 426. The "Super Prescription" is communicated to all appropriate pharmacies that meet the patient's criteria. The bidding pharmacies return the bid with key fields completed, a unique tracking number and contact information. The system compiles the bid results and the physician's staff prints the report for the patient.

Figure 10:
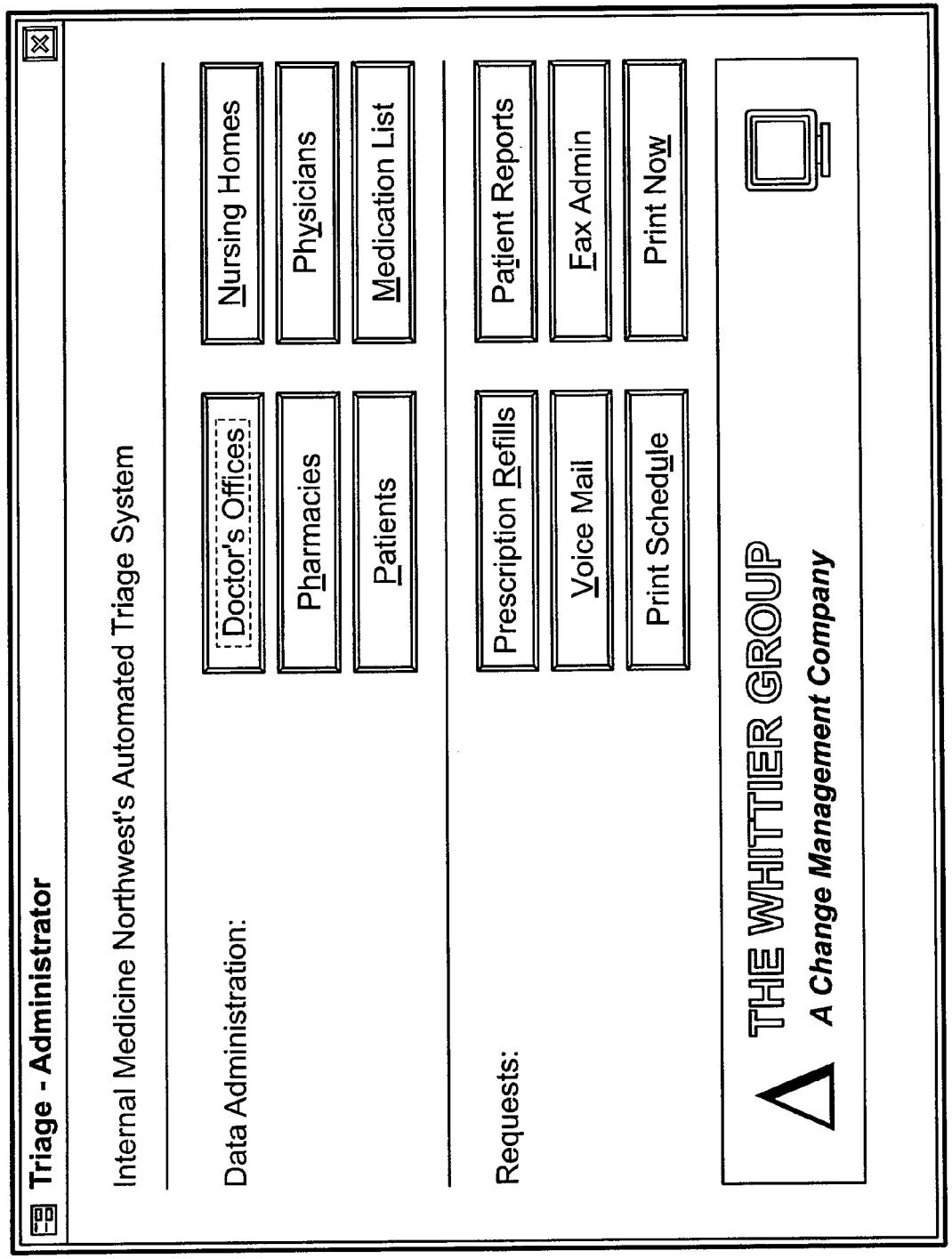
FIG. 10 is a computer screen image of the Triage Administrator.

FIG. 10 illustrates the Triage Administrator, the graphical user interface for the program. There are two parts to the Triage Administrator, the Data Administrator and the Requests Administrator. The Data Administrator, located on the top portion of the Administrator application, links to MS Access databases that store the Doctors Office, Nursing Home, Pharmacy, Physician, Patients and Medication NDC Information. From the Data Administrator users can search and update the databases. Simply click on the database you would like to open and an interface menu will appear. Using this menu you can add and delete records, search for a particular record or create voice tags for entries if you do not like the current computer generated speech. The bottom half of the Triage Administrator, the Request Administrator, handles all executable functions. The Request Administrator allows users to fill prescription requests, listen to voice mail from nursing homes, print all prescription refill requests to the default printer, fill patient report requests and check the status of outgoing faxes.

FIG. 11 illustrates the Prescription Refill Request screen that displays all captured information for a refill request. The user uses one of the 5 buttons to approve the request or take another action. The system administrator can customize the text of these buttons. The user also has the option of typing a free text message in the comments box. Once the user completes the refill request the user can select the Fax Reply button to send the fax to the Pharmacy that called in the prescription refill request. The fax will be sent to the telephone number listed on the right hand side of the request labeled "Fax Number." Alternatively, the user can select the print button and the prescription refill request will be printed to the default printer. Also, internet protocols have been added to this service which make it possible to e-mail the request.

Figure 12:
FIG. 12 is a computer screen image of the Patient Reports Request.

FIG. 12 refers to the Patient Reports Request that displays all the captured information for a Patient Reports request. This form is used as the response cover sheet with the required records attached to the outgoing e-mail or fax.

Figure 13:
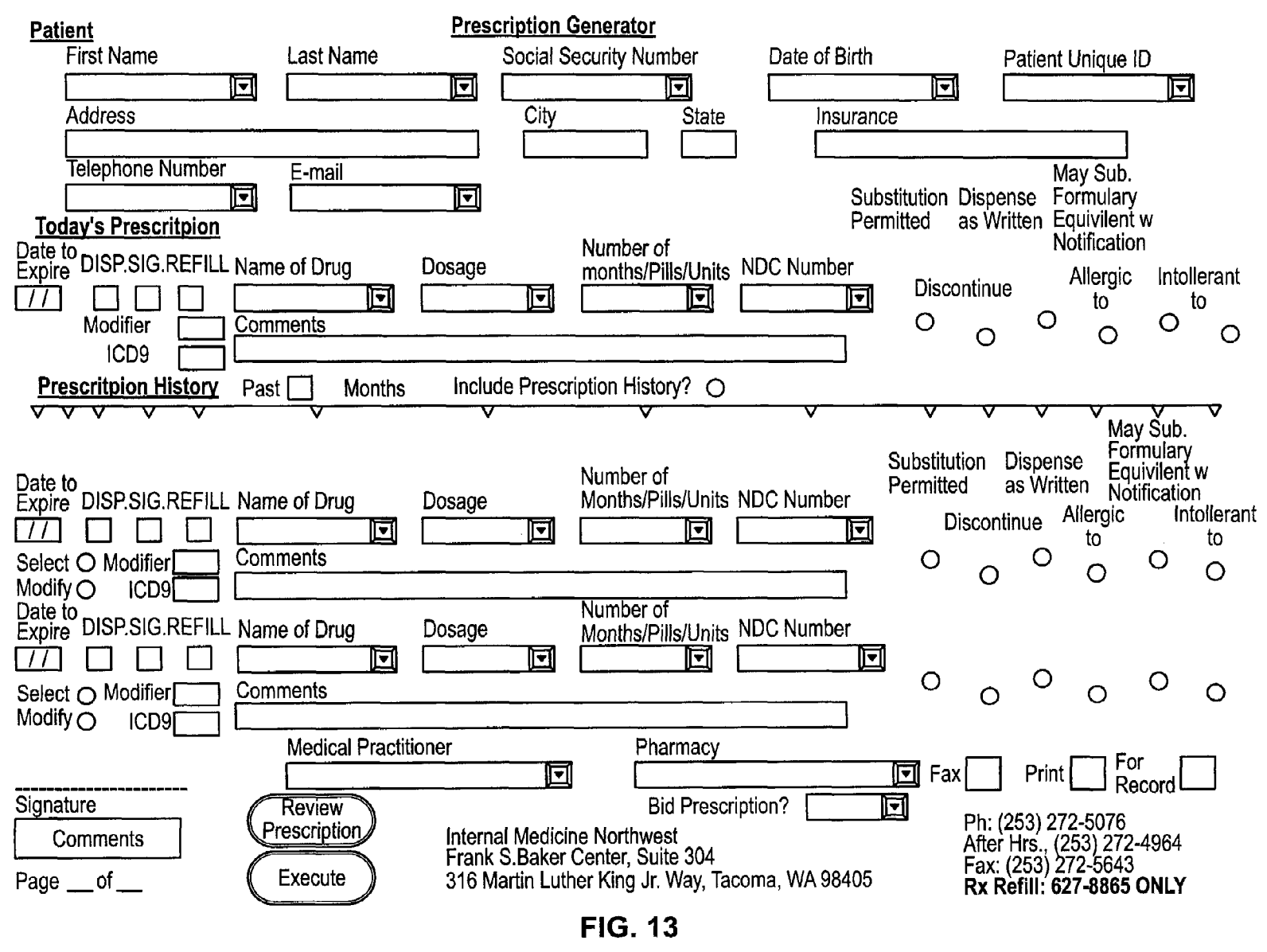

FIG. 13 refers to the user interface for the New Prescription service of the Triage Administrator. The physician completes the required fields in order to generate a new prescription or "Super Prescription." The specific steps for completing this form are detailed in the explanation of FIGS. 8A and 8B.

Figure 14:
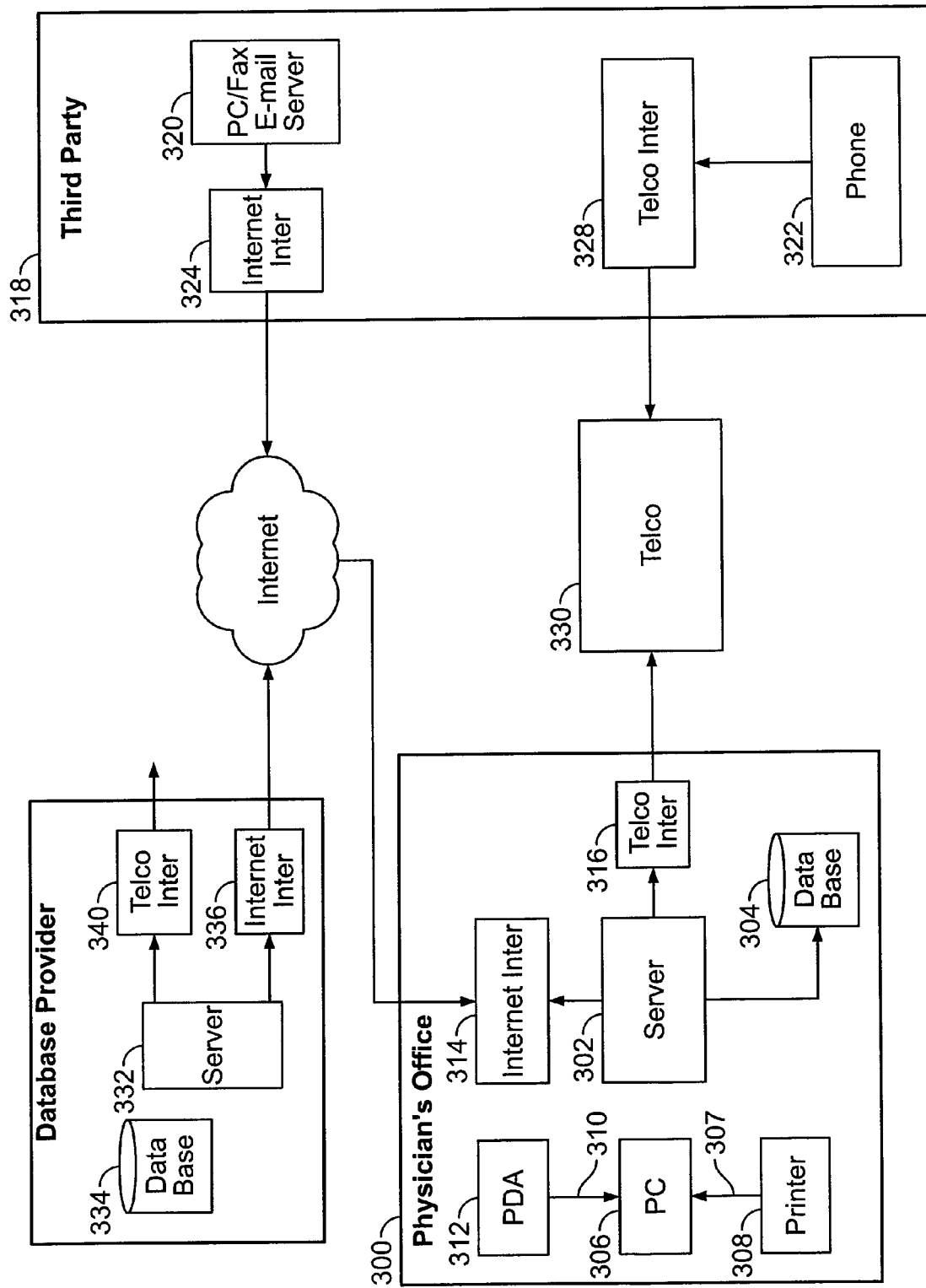
FIG. 14 is a block diagram of the system of the present invention.

FIG. 14 is a block diagram of the system of the present invention. A physician's office 300 includes a server 302 and a database 304 which provides the patient's records. A PC 306 in the physician's office is connected via a link 304 to the server 302 and includes a link 306 to a printer 308 as well as a link 310 to a PDA 312. The link 310 to the PDA 312 maybe a hard wire connection or a wireless connection. The server 302 includes an internet interface 314 and a telephone company interface 316. A third party site 318, such as a pharmacy, hospital, emergency room or other physician site, is shown to include a personal computer 320 and a phone 322. The personal computer 320 includes an internet interface 324 for connection to the internet 326. The phone 322 includes a telephone company interface 328 for connection to telephone lines 330, as is known in the art. In this matter, the third party may gain access to the interactive voice response system resident in the server 302 in the physician's office 300. A report may be sent by the physician's office via the internet to the third party PC 320. The third party PC 320 may include a fax and/or email server.

In the alternative, the physician's office may omit the server 302 and database 304. Rather, the physician's office may obtain patients' record on the server 332 and database 334 of the database provider 336. The physician's office may gain access to the database 334 via the internet interface 338. The third parties may obtain records from the database provider 336 via telephone company interface 340.

In the embodiment wherein the physician's office does not include a server and database, the office PC 306 may include the internet and telephone company interfaces 314, 316.

In the embodiment wherein the server 302 and database 304 are resident at the physician's office, it will be apparent that the link 304 may be a network for coupling to multiple pc's located throughout the physician's office.

While the preferred embodiment of this invention has been shown and described, it will be apparent to those skilled in the art that changes and modifications may be made therein without departing from the spirit of the invention, the scope of which is defined by the appended claims.

What is claimed is:

1. A method of processing a prescription refill request via an interactive voice response system, the method comprising the steps of:

receiving a refill request for a patient and received at a pharmacy;
providing access for a pharmacy to the interactive voice response system for obtaining approval of the refill request from a physician;
prompting the pharmacy for a first indicator, wherein the first indicator is at least one of:
a pharmacy phone number,
at least a portion of the patient's name, and
a NDC number,
wherein the first indicator indicates information, wherein the information includes at least one of:
a pharmacy identification;
a patient identification; and
identification of a medication corresponding to the prescription to be filled,
wherein prompting the pharmacy for the first indicator of information includes audibly prompting the pharmacy by reciting a statement of words to the pharmacy that describes the first indicator of the information;
in response to receiving the first indicator from the pharmacy, retrieving by the system, from a database, a second indicator of the same information indicated by the first indicator;
audibly reciting the second indicator to the pharmacy;
confirming, by the pharmacy, that the second indicator is correct,
wherein confirming the second indicator is correct confirms that the first indicator identified the correct information;
providing the refill request from the pharmacy to the physician after the pharmacy confirms the second indicator is correct; and
receiving, by the pharmacy, the approval of the refill request from the physician.

2. The method of claim 1, further comprising the step of displaying both a NDC number and the name of the medication to a physician for providing an authorization for the requested refill.

3. The method of claim 1, further comprising at least one of:
wherein when the first indicator is a pharmacy phone number, the second indicator is the name of the pharmacy for confirming the pharmacy identification,
wherein when the first indicator is at least a portion of a patient's names, the second indicator is a full name of the patient for confirming the patient identifications, and
wherein when the first indicator is a NDC number, the second indicator is at least one of a generic name and a commercial name of the medication for confirming the medication.

4. The method of claim 1, further comprising at least one of the steps of:
prompting for the date the prescription was last filled;
prompting for the identification of the original prescribing physician; and
prompting for the quantity of the medication.

5. The method of claim 1, wherein each response to a prompt is followed by a confirmation of the response and the prescription refill request is assigned a unique tracking identification.

6. The method of claim 1, further comprising the steps of:
creating a database entry for each prescription refill request, the database entry including a NDC identification and a corresponding commercial or generic name of the medication corresponding to the NDC identification, whereby a physician or individual may consider and provide the refill authorization based on the commercial or generic name of the medication.

7. The method of claim 6, further comprising at least one of the steps of:
providing a physician or other user access to the database entry;
prompting the physician or other user for the confirmation that the requested prescription is compatible with other medications, if any, prescribed to the patient;
prompting the physician or other user to enter comments;
prompting the physician or other user to indicate approval of the request; and
prompting the physician or other user to dispatch the indication of approval and corresponding comments, if any, to the requesting pharmacy.

8. An interactive voice response system of processing a prescription refill request, the system comprising:
means for providing access to an interactive response system for a pharmacy to obtain approval of refill requests received for a patient, and received by the pharmacy, and wherein the approval is to be obtained from a physician;
a database having information identifiable by at least a first and second indicator, wherein the information is at least one of:
a pharmacy identification,
a patient identification, and
an identification of a medication corresponding to the prescription to be filled, and
wherein the first indicator is at least one of:
a pharmacy phone number,
at least a portion of the patient's name, and
a NDC number;
means for prompting the pharmacy for the first indicator of the information including a first audible statement of words received by the pharmacy and being a description of the first indicator of the information;
means for determining the second indicator of the information in response to receiving the first indicator;
a second audible statement of words received by the pharmacy and reciting the second indicator of the information indicated by the first indicator;
means for the pharmacy to confirm that the second indicator is correct, wherein confirming the second indicator is correct also acts to confirm the first indicator identified the correct information;
means for providing the refill request to a physician after the pharmacy confirms the second indicator is correct;
means for receiving the approval of the refill request from the physician.

9. The system of claim 8, further comprising:
means for creating a database entry for each prescription refill request, the database entry including a NDC identification and a corresponding commercial or generic name of the medication corresponding to the NDC identification, whereby a physician or individual may consider and provide the refill authorization based on the commercial or generic name of the medication.

10. The method of claim 1, further comprising prompting the pharmacy for the first indicator for each of the pharmacy identification, the patient identification, and the identification of a medication, wherein prompting for each first indicator includes audibly prompting the pharmacy.

11. The method of claim 1, further including the steps of responding to the prompting steps by using a keypad on a telecommunication device.

12. The method of claim 1, further comprising the step of permitting the pharmacy to obtain refill information through the interactive voice response system only if the second indicator is correct.

13. A method of processing a prescription refill request comprising the step of:
receiving a refill request for a patient and received by a pharmacy;
audibly prompting the pharmacy by a statement of words requesting a first indicator of information related to the refill request, wherein the information is at least one of:
a pharmacy identification,
a patient identification, and
identification of a medication corresponding to the prescription to be filled, and wherein the first indicator is at least one of:
a pharmacy phone number,
at least a portion of the patient's name, and
a NDC number;
providing the first indicator by using a keypad on a telecommunication device;
in response to receiving the first indicator from the pharmacy, using the first indicator to look up the information;
retrieving a second indicator of the same information indicated by the first indicator;
audibly reciting the second indicator of the information to the pharmacy:
answering, by the pharmacy, whether or not the audible statement reciting the second indicator is correct by using a keypad, wherein confirming the second indicator is correct acts to confirm that the first indicator identified the correct information;
displaying the refill request to a physician required to approve or deny the refill request; and
receiving approval of the refill request from the physician.

14. The method of claim 13, wherein when the first indicator is the pharmacy's phone number, the second indicator is the name of the pharmacy.

15. The method of claim 13, wherein when the first indicator is at least a portion of a patient's name or patient's date of birth, the second indicator is the patient's full name.

16. The method of claim 13, wherein when the first indicator is the NDC number of the medication requested for the refill request, the second indicator is the name of the medication.

17. The method of claim 13, wherein both a NDC number and the name of the medication is displayed to the physician.

\* \* \* \* \*

UNITED STATES PATENT AND TRADEMARK OFFICE
CERTIFICATE OF CORRECTION

| | |
|---|---|
| PATENT NO. | : 7,426,476 B2 |
| APPLICATION NO. | : 09/818168 |
| DATED | : September 16, 2008 |
| INVENTOR(S) | : Munoz et al. |

It is certified that error appears in the above-identified patent and that said Letters Patent is hereby corrected as shown below:

In Claim 3, Column 14, Line 46, delete "names" and insert -- name --, therefor.

In Claim 3, Column 14, Line 47, delete "identifications" and insert -- identification --, therefor.

In Claim 29, Column 16, Line 14, delete "step" and insert -- steps --, therefor.

In Claim 29, Column 16, Line 35, delete ":" and insert -- ; --, therefor.

Signed and Sealed this

Thirtieth Day of December, 2008

JON W. DUDAS
*Director of the United States Patent and Trademark Office*